(12) United States Patent
Peterson et al.

(10) Patent No.: US 9,717,815 B2
(45) Date of Patent: Aug. 1, 2017

(54) AIR FRESHENER DISPENSERS, CARTRIDGES THEREFOR, SYSTEMS, AND METHODS

(71) Applicant: Georgia-Pacific Consumer Products LP, Atlanta, GA (US)

(72) Inventors: Eric Paul Peterson, Hortonville, WI (US); Todd Richard Lappi, Atlanta, GA (US); Daniel M. D'Amico, South Salem, NY (US); John Patrick Laitala, Appleton, WI (US); Ryan David Carignan, Oshkosh, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 116 days.

(21) Appl. No.: 14/812,599

(22) Filed: Jul. 29, 2015

(65) Prior Publication Data
US 2016/0030620 A1   Feb. 4, 2016

Related U.S. Application Data

(60) Provisional application No. 62/030,780, filed on Jul. 30, 2014.

(51) Int. Cl.
*B01F 3/04*   (2006.01)
*A61L 9/12*   (2006.01)
(Continued)

(52) U.S. Cl.
CPC .............. *A61L 9/122* (2013.01); *A61L 9/012* (2013.01); *B01D 47/00* (2013.01); *B01F 3/04* (2013.01); *A61L 2209/111* (2013.01)

(58) Field of Classification Search
CPC ............. B01F 3/04; B01D 47/00; A61L 9/122
(Continued)

(56) References Cited

U.S. PATENT DOCUMENTS 2,539,059 A   1/1951   Cohn
2,546,820 A   3/1951   Grant
(Continued)

FOREIGN PATENT DOCUMENTS

CN   101260331 A   9/2008
DE   10324567 A1   12/2004
(Continued)

OTHER PUBLICATIONS

International Search Report and Written Opinion for International Application No. PCT/US2015/042757 mailed Nov. 5, 2015 (14 pages).

*Primary Examiner* — Robert A Hopkins
(74) *Attorney, Agent, or Firm* — Eversheds Sutherland (US) LLP

(57) ABSTRACT

Automated air freshener dispensers and cartridges therefor are provided herein. Air freshener dispensers include a housing having a cavity for receiving a cartridge containing an air freshening substance for release, a fan that induces an airflow through the housing and directs the airflow to an area outside of the air freshener dispenser, such that released air freshening substance is entrained in the airflow, a motor for driving the fan, at least one sensor, and a controller that receives a signal from the at least one sensor and directs operation of the fan in response thereto.

19 Claims, 28 Drawing Sheets

(51) Int. Cl.
  *B01D 47/00* (2006.01)
  *A61L 9/012* (2006.01)
(58) Field of Classification Search
  USPC ............... 261/26, 30, DIG. 88; 422/124
  See application file for complete search history.

(56) References Cited

U.S. PATENT DOCUMENTS

| | | |
|---|---|---|
| 2,728,604 A | 12/1955 | Garfield |
| 3,151,822 A | 10/1964 | Glaner |
| 3,192,008 A | 6/1965 | Dwyer |
| 3,930,696 A | 1/1976 | Hight et al. |
| 3,994,439 A | 11/1976 | Van Breen et al. |
| 4,035,451 A | 7/1977 | Tringali |
| 4,071,564 A | 1/1978 | Bauer et al. |
| 4,110,430 A | 8/1978 | Hopp et al. |
| 4,251,448 A | 2/1981 | Bauer et al. |
| 4,254,179 A | 3/1981 | Carson, III et al. |
| 4,263,459 A | 4/1981 | Bauer et al. |
| 4,492,644 A | 1/1985 | Matsumoto et al. |
| 4,521,541 A | 6/1985 | Rutherford et al. |
| 4,523,023 A | 6/1985 | Finkelmeier et al. |
| 4,543,367 A | 9/1985 | Rutherford et al. |
| 4,552,693 A | 11/1985 | Hussain et al. |
| 4,598,664 A | 7/1986 | Hamlin |
| 4,632,837 A | 12/1986 | Schütz et al. |
| 4,695,435 A * | 9/1987 | Spector .................. A61L 9/122 239/54 |
| 4,735,626 A | 4/1988 | Smith et al. |
| 4,759,510 A | 7/1988 | Singer |
| 4,931,224 A | 6/1990 | Holzner, Sr. |
| 4,991,538 A | 2/1991 | Davids et al. |
| 5,079,783 A | 1/1992 | Haletsky et al. |
| 5,105,005 A | 4/1992 | Hopp et al. |
| 5,114,625 A | 5/1992 | Gibson |
| 5,126,078 A | 6/1992 | Steiner et al. |
| 5,147,582 A | 9/1992 | Holzner, Sr. et al. |
| 5,170,938 A | 12/1992 | Dewing |
| 5,212,153 A | 5/1993 | Hopp et al. |
| 5,248,831 A | 9/1993 | Hopp et al. |
| 5,260,459 A | 11/1993 | Brunke et al. |
| 5,294,602 A | 3/1994 | Brunke et al. |
| 5,342,584 A | 8/1994 | Fritz et al. |
| 5,370,829 A | 12/1994 | Kunze |
| 5,426,095 A | 6/1995 | Brunke et al. |
| 5,431,885 A | 7/1995 | Zlotnik et al. |
| 5,494,218 A | 2/1996 | Armand |
| 5,595,303 A | 1/1997 | Weeks et al. |
| 5,624,025 A | 4/1997 | Hixon |
| 5,672,206 A | 9/1997 | Gorman |
| 5,693,606 A | 12/1997 | Brunke et al. |
| 5,695,692 A | 12/1997 | Kennedy |
| 5,697,684 A | 12/1997 | Gyovai |
| 5,707,696 A | 1/1998 | Boxler |
| 5,725,822 A | 3/1998 | Keller et al. |
| 5,735,918 A | 4/1998 | Barradas |
| 5,775,876 A | 7/1998 | Walker et al. |
| 5,830,846 A | 11/1998 | Bertram et al. |
| 5,851,106 A | 12/1998 | Steiner et al. |
| 5,857,621 A | 1/1999 | Poulos |
| 5,951,970 A | 9/1999 | Wrede et al. |
| 5,972,878 A | 10/1999 | Sonnenberg et al. |
| 5,997,901 A | 12/1999 | Mills |
| 6,000,658 A | 12/1999 | McCall, Jr. |
| 6,034,052 A | 3/2000 | Körber et al. |
| 6,109,874 A | 8/2000 | Steiner et al. |
| 6,190,607 B1 | 2/2001 | Farmer |
| 6,313,306 B1 | 11/2001 | Engel et al. |
| 6,357,726 B1 | 3/2002 | Watkins |
| 6,371,450 B1 | 4/2002 | Davis et al. |
| 6,391,234 B1 | 5/2002 | Silvi et al. |
| 6,392,054 B1 | 5/2002 | Güntert et al. |
| 6,403,075 B1 | 6/2002 | Costa |
| 6,406,734 B1 | 6/2002 | Albanese et al. |
| 6,457,434 B1 | 10/2002 | Lazar |
| 6,511,531 B1 | 1/2003 | Cartellone |
| 6,557,797 B1 | 5/2003 | Bonamarte |
| 6,575,383 B2 | 6/2003 | Dobler et al. |
| 6,631,852 B1 | 10/2003 | O'Leary |
| 6,644,507 B2 | 11/2003 | Borut et al. |
| 6,688,551 B1 | 2/2004 | He et al. |
| 6,741,954 B2 | 5/2004 | Sonnenberg et al. |
| 6,783,117 B2 | 8/2004 | Wohrle |
| 6,815,413 B2 | 11/2004 | Eh et al. |
| 6,883,787 B2 | 4/2005 | Allen |
| 6,914,109 B2 | 7/2005 | Kuhn et al. |
| 6,969,024 B2 | 11/2005 | He et al. |
| 7,104,755 B2 | 9/2006 | Owens et al. |
| 7,108,803 B1 | 9/2006 | Mansfeld et al. |
| 7,129,380 B2 | 10/2006 | Reckziegel et al. |
| 7,157,411 B2 | 1/2007 | Rohde et al. |
| 7,188,783 B2 | 3/2007 | Ivey et al. |
| 7,204,870 B2 | 4/2007 | Zobele et al. |
| 7,220,288 B2 | 5/2007 | D'Amico et al. |
| 7,234,648 B2 | 6/2007 | Tepper et al. |
| 7,235,261 B2 | 6/2007 | Smith et al. |
| 7,247,295 B2 | 7/2007 | Schmaus et al. |
| 7,332,468 B2 | 2/2008 | Widder et al. |
| 7,344,123 B2 | 3/2008 | Pankhurst et al. |
| 7,378,121 B2 | 5/2008 | Ley et al. |
| 7,410,513 B2 | 8/2008 | Requejo et al. |
| 7,439,403 B2 | 10/2008 | Hölscher |
| 7,481,571 B2 | 1/2009 | Bistritzky et al. |
| 7,485,610 B2 | 2/2009 | Heinz et al. |
| 7,494,967 B2 | 2/2009 | Dilk et al. |
| 7,549,598 B2 | 6/2009 | Tepper et al. |
| 7,569,733 B2 | 8/2009 | Brocke et al. |
| 7,581,717 B1 | 9/2009 | Thurlkill |
| 7,615,526 B2 | 11/2009 | Hoelscher |
| 7,648,127 B2 | 1/2010 | Cittadino |
| D612,914 S | 3/2010 | Morad |
| 7,748,687 B2 | 7/2010 | Pankhurst et al. |
| 7,763,238 B2 | 7/2010 | Preti et al. |
| 7,846,886 B2 | 12/2010 | Oertling et al. |
| 7,884,065 B2 | 2/2011 | Reckziegel et al. |
| 7,887,759 B2 | 2/2011 | Triplett |
| 7,905,426 B1 | 3/2011 | Greiner |
| 8,007,707 B1 | 8/2011 | Brown et al. |
| 8,043,569 B2 | 10/2011 | Tranzeat |
| 8,043,606 B2 | 10/2011 | MacBeath et al. |
| 8,048,379 B2 | 11/2011 | Sassoon |
| 8,074,970 B2 | 12/2011 | Pankhurst et al. |
| 8,119,072 B2 | 2/2012 | D'Amico |
| 8,226,931 B2 | 7/2012 | Kindel et al. |
| D665,064 S | 8/2012 | D'Amico |
| 8,318,711 B2 | 11/2012 | Gatfield et al. |
| 8,372,349 B1 | 2/2013 | Shotey et al. |
| 8,414,834 B2 | 4/2013 | Gorman |
| 8,513,180 B2 | 8/2013 | Wiedemann et al. |
| 8,524,158 B2 | 9/2013 | Shi et al. |
| 8,584,982 B2 | 11/2013 | Eakin |
| 8,603,397 B2 | 12/2013 | Gruenbacher et al. |
| 8,673,223 B1 | 3/2014 | Finlay |
| 8,747,755 B2 | 6/2014 | Larsson |
| 8,759,279 B2 | 6/2014 | Funk et al. |
| 8,916,140 B2 | 12/2014 | MacBeath et al. |
| 8,927,617 B2 | 1/2015 | Funk et al. |
| 8,974,736 B2 | 3/2015 | Brown et al. |
| 8,991,647 B2 | 3/2015 | Meyers |
| 9,107,969 B2 | 8/2015 | Lezniak et al. |
| D742,497 S | 11/2015 | D'Amico et al. |
| D749,203 S | 2/2016 | D'Amico et al. |
| 9,278,152 B2 | 3/2016 | Irwin et al. |
| 2002/0123437 A1 | 9/2002 | Conboy et al. |
| 2002/0137660 A1 | 9/2002 | Kuhn et al. |
| 2002/0146441 A1 | 10/2002 | Sonnenberg et al. |
| 2002/0192174 A1 | 12/2002 | Kawakami et al. |
| 2002/0197189 A1 | 12/2002 | Lua |
| 2003/0087774 A1 | 5/2003 | Smith et al. |
| 2003/0107139 A1 | 6/2003 | Wohrle |
| 2003/0199412 A1 | 10/2003 | Gupta et al. |
| 2003/0202922 A1 * | 10/2003 | Farmer .................. A61L 9/042 422/306 |
| 2004/0037799 A1 | 2/2004 | Costa et al. |

(56) References Cited

U.S. PATENT DOCUMENTS

| | | |
|---|---|---|
| 2004/0094635 A1 | 5/2004 | Harris et al. |
| 2004/0186042 A1 | 9/2004 | Schmaus et al. |
| 2004/0265164 A1 | 12/2004 | Woo et al. |
| 2005/0079113 A1* | 4/2005 | Selander ............... A61L 9/122 422/306 |
| 2005/0169813 A1 | 8/2005 | D'Amico et al. |
| 2005/0191217 A1 | 9/2005 | Selander |
| 2005/0224594 A1 | 10/2005 | Wolf |
| 2006/0009372 A1 | 1/2006 | Mansfeld et al. |
| 2006/0039835 A1 | 2/2006 | Nottingham et al. |
| 2006/0074742 A1 | 4/2006 | Santandrea |
| 2006/0110297 A1 | 5/2006 | D'Amico et al. |
| 2006/0251541 A1 | 11/2006 | Santandrea |
| 2007/0023564 A1 | 2/2007 | Platt |
| 2007/0025798 A1 | 2/2007 | Platt |
| 2007/0036673 A1 | 2/2007 | Selander |
| 2007/0108759 A1 | 5/2007 | D'Amico |
| 2007/0160492 A1 | 7/2007 | Spector |
| 2007/0217945 A1 | 9/2007 | Selander |
| 2007/0218179 A1 | 9/2007 | Ott et al. |
| 2007/0254826 A1 | 11/2007 | Kindel et al. |
| 2007/0258849 A1 | 11/2007 | Kent |
| 2007/0297993 A1 | 12/2007 | Kindel et al. |
| 2007/0298994 A1 | 12/2007 | Finke et al. |
| 2008/0032913 A1 | 2/2008 | Finke et al. |
| 2008/0060119 A1 | 3/2008 | Pinizzotto |
| 2008/0199367 A1 | 8/2008 | Lin |
| 2008/0220140 A1 | 9/2008 | Ley et al. |
| 2008/0242740 A1 | 10/2008 | Ley et al. |
| 2008/0317923 A1 | 12/2008 | Ley et al. |
| 2009/0001213 A1 | 1/2009 | Looft |
| 2009/0064585 A1 | 3/2009 | Mansfeld et al. |
| 2009/0110654 A1 | 4/2009 | Hagemann et al. |
| 2009/0117012 A1 | 5/2009 | Bankers et al. |
| 2009/0162308 A1 | 6/2009 | Kuhn et al. |
| 2009/0224205 A1 | 9/2009 | Braun et al. |
| 2009/0224206 A1 | 9/2009 | Braun et al. |
| 2009/0283722 A1 | 11/2009 | Braun et al. |
| 2009/0293916 A1 | 12/2009 | Wiedemann |
| 2010/0001417 A1 | 1/2010 | D'Amico |
| 2010/0068092 A1 | 3/2010 | Larsson |
| 2010/0129268 A1 | 5/2010 | Andersen |
| 2010/0130624 A1 | 5/2010 | Oertling |
| 2010/0163801 A1 | 7/2010 | Braun et al. |
| 2010/0233102 A1 | 9/2010 | Krammer et al. |
| 2010/0243754 A1 | 9/2010 | Harris |
| 2010/0284783 A1 | 11/2010 | Lolmede |
| 2010/0309434 A1 | 12/2010 | Van Schijndel et al. |
| 2010/0310492 A1 | 12/2010 | Stalet et al. |
| 2010/0320282 A1 | 12/2010 | Sissom |
| 2010/0331349 A1 | 12/2010 | Ley et al. |
| 2011/0004986 A1 | 1/2011 | Vu |
| 2011/0027124 A1 | 2/2011 | Albee et al. |
| 2011/0041241 A1 | 2/2011 | Frank |
| 2011/0091404 A1 | 4/2011 | Wöhrle et al. |
| 2011/0095097 A1 | 4/2011 | Herd et al. |
| 2011/0104089 A1 | 5/2011 | Wöhrle et al. |
| 2011/0114663 A1 | 5/2011 | Brown et al. |
| 2011/0129432 A1 | 6/2011 | Hillers et al. |
| 2011/0155616 A1 | 6/2011 | Eh et al. |
| 2011/0293538 A1 | 12/2011 | Ley et al. |
| 2011/0318296 A1 | 12/2011 | Braun et al. |
| 2012/0101020 A1 | 4/2012 | Wiedemann et al. |
| 2012/0107172 A1 | 5/2012 | Ono et al. |
| 2012/0107258 A1 | 5/2012 | Kuhn et al. |
| 2012/0181350 A1 | 7/2012 | Snider |
| 2012/0248136 A1 | 10/2012 | Meyers |
| 2012/0273586 A1 | 11/2012 | Shook et al. |
| 2012/0298686 A1 | 11/2012 | Mothaffar |
| 2013/0049236 A1 | 2/2013 | Garon et al. |
| 2013/0056552 A1 | 3/2013 | Teeling et al. |
| 2013/0309102 A1 | 11/2013 | Gruenbacher et al. |
| 2013/0327845 A1 | 12/2013 | Lesniak et al. |
| 2014/0076989 A1 | 3/2014 | Granger et al. |
| 2014/0076991 A1 | 3/2014 | Irwin et al. |
| 2014/0103133 A1 | 4/2014 | Muderlak et al. |
| 2014/0115767 A1 | 5/2014 | Muderlak et al. |
| 2014/0117114 A1 | 5/2014 | Muderlak et al. |
| 2014/0157501 A1 | 6/2014 | D'Amico |

FOREIGN PATENT DOCUMENTS

| | | |
|---|---|---|
| DE | 102004038880 A1 | 3/2006 |
| DE | 102007000757 A1 | 4/2009 |
| EP | 0115007 A1 | 8/1984 |
| EP | 0360084 A1 | 3/1990 |
| EP | 0908188 A2 | 4/1999 |
| EP | 1479400 A1 | 11/2004 |
| EP | 1927646 A1 | 6/2008 |
| EP | 2075321 A1 | 7/2009 |
| EP | 2287158 A1 | 2/2011 |
| GB | 1014047 A | 12/1965 |
| JP | 4019394 A | 1/1992 |
| JP | 2001303090 A | 10/2001 |
| JP | 2003320003 A | 11/2003 |
| JP | 2003321697 A | 11/2003 |
| KR | 20060086444 A | 7/2006 |
| WO | 96/31741 A1 | 10/1996 |
| WO | 98/30621 A1 | 7/1998 |
| WO | 98/46280 A1 | 10/1998 |
| WO | 00/53301 A1 | 9/2000 |
| WO | 01/38440 A1 | 5/2001 |
| WO | 02/076516 A1 | 3/2002 |
| WO | 02/066084 A1 | 8/2002 |
| WO | 02/072161 A1 | 9/2002 |
| WO | 03/028775 A1 | 4/2003 |
| WO | 03/049713 A1 | 6/2003 |
| WO | 03/070871 A1 | 8/2003 |
| WO | 03/097629 A1 | 11/2003 |
| WO | 2004/002930 A1 | 1/2004 |
| WO | 2004/015036 A1 | 2/2004 |
| WO | 2004/015037 A1 | 2/2004 |
| WO | 2004/015038 A1 | 2/2004 |
| WO | 2004/015039 A1 | 2/2004 |
| WO | 2004/015040 A1 | 2/2004 |
| WO | 2004/024853 A1 | 3/2004 |
| WO | 2004/093929 A2 | 11/2004 |
| WO | 2004/096588 A2 | 11/2004 |
| WO | 2005/063944 A1 | 7/2005 |
| WO | 2005/063945 A1 | 7/2005 |
| WO | 2006/040292 A1 | 4/2006 |
| WO | 2006/079607 A1 | 8/2006 |
| WO | 2006/105347 A1 | 10/2006 |
| WO | 2007/060048 A1 | 5/2007 |
| WO | 2007/073953 A1 | 7/2007 |
| WO | 2008/017598 A2 | 2/2008 |
| WO | 2008/017604 A1 | 2/2008 |
| WO | 2008/030761 A2 | 3/2008 |
| WO | 2008/050921 A1 | 5/2008 |
| WO | 2008/066426 A1 | 6/2008 |
| WO | 2008/112545 A1 | 9/2008 |
| WO | 2009/040788 A2 | 4/2009 |
| WO | 2009/061976 A1 | 5/2009 |
| WO | 2009/087118 A1 | 7/2009 |
| WO | 2009/092135 A1 | 7/2009 |
| WO | 2009/101571 A1 | 8/2009 |
| WO | 2010-132565 A1 | 11/2010 |
| WO | 2010/142469 A1 | 12/2010 |
| WO | 2010/142815 A2 | 12/2010 |
| WO | 2011/001808 A1 | 1/2011 |
| WO | 2012/055785 A1 | 5/2012 |
| WO | 2012/055875 A1 | 5/2012 |
| WO | 2012/093246 A1 | 7/2012 |
| WO | 2013/147723 A2 | 10/2013 |

* cited by examiner

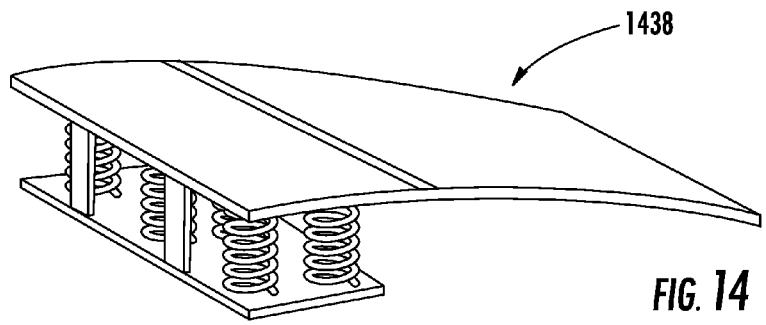
FIG. 14
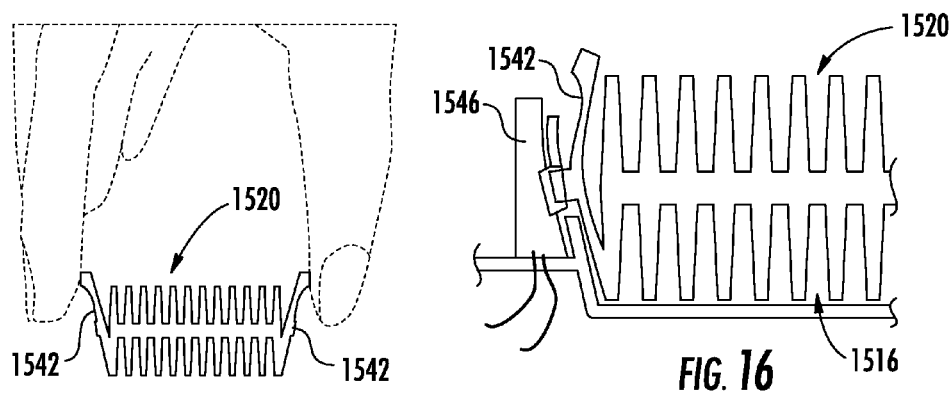
FIG. 15
FIG. 16
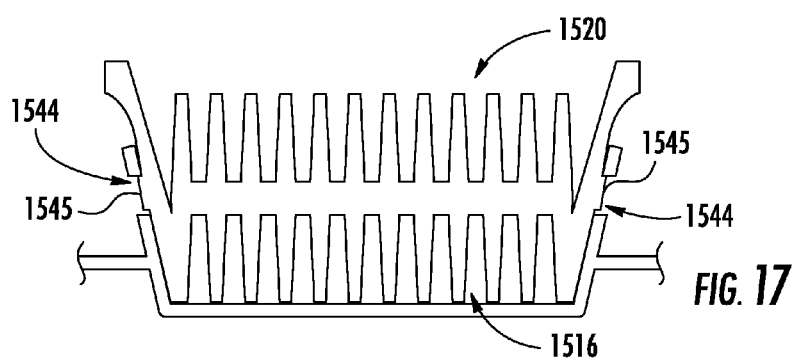
FIG. 17

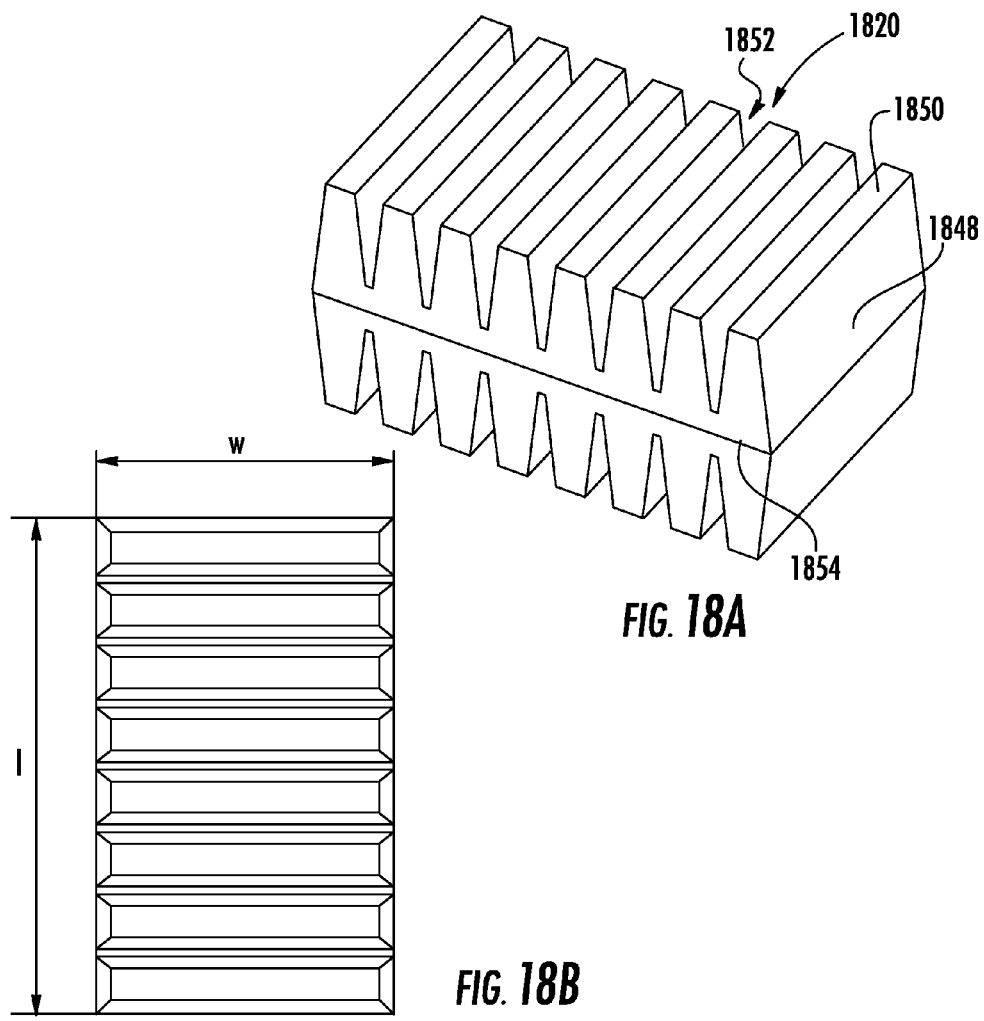
FIG. 18A
FIG. 18B
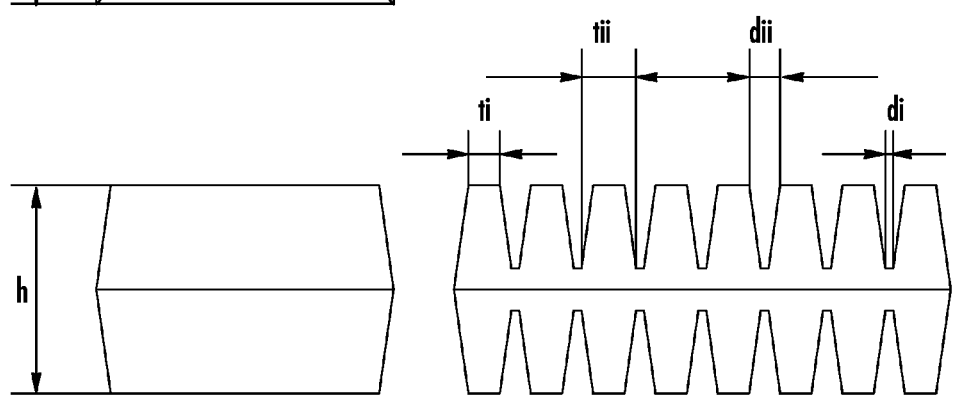
FIG. 18C
FIG. 18D

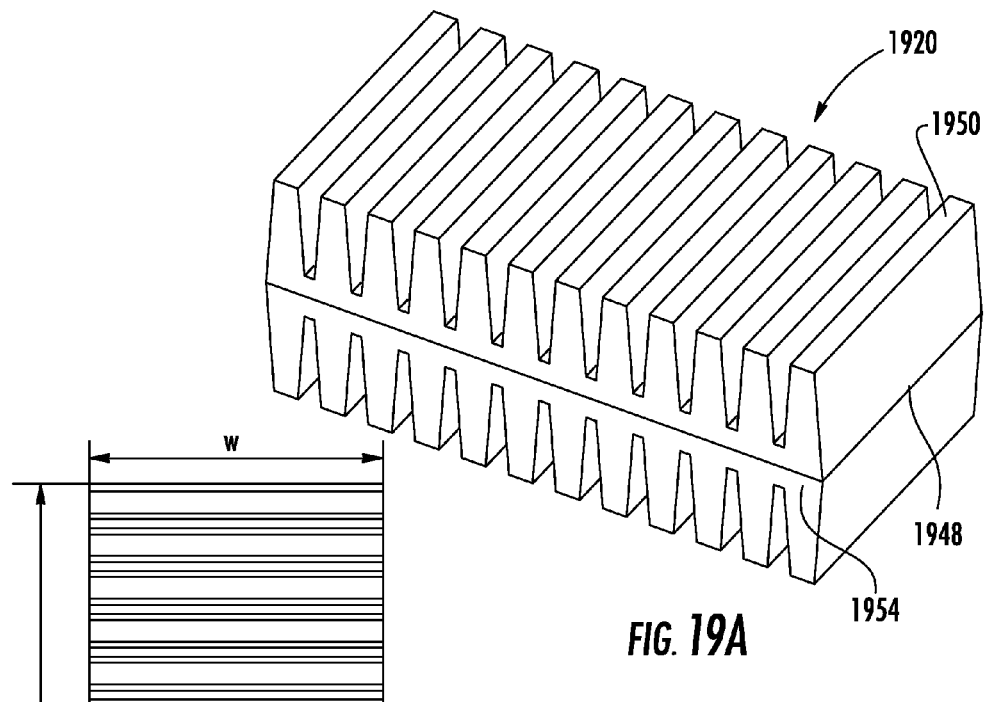
FIG. 19A
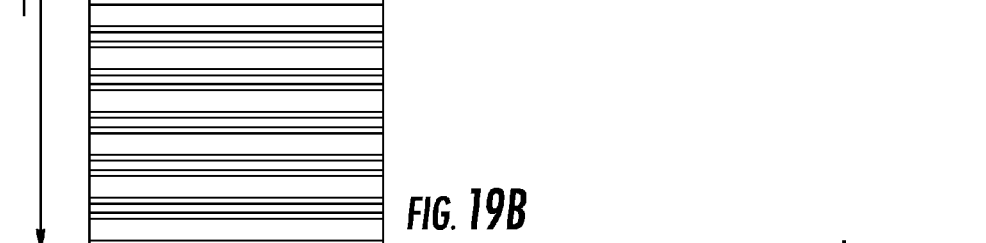
FIG. 19B
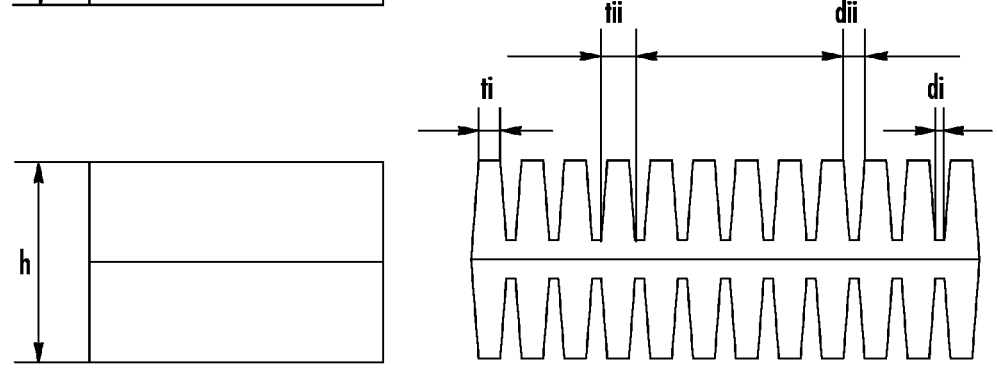
FIG. 19C
FIG. 19D

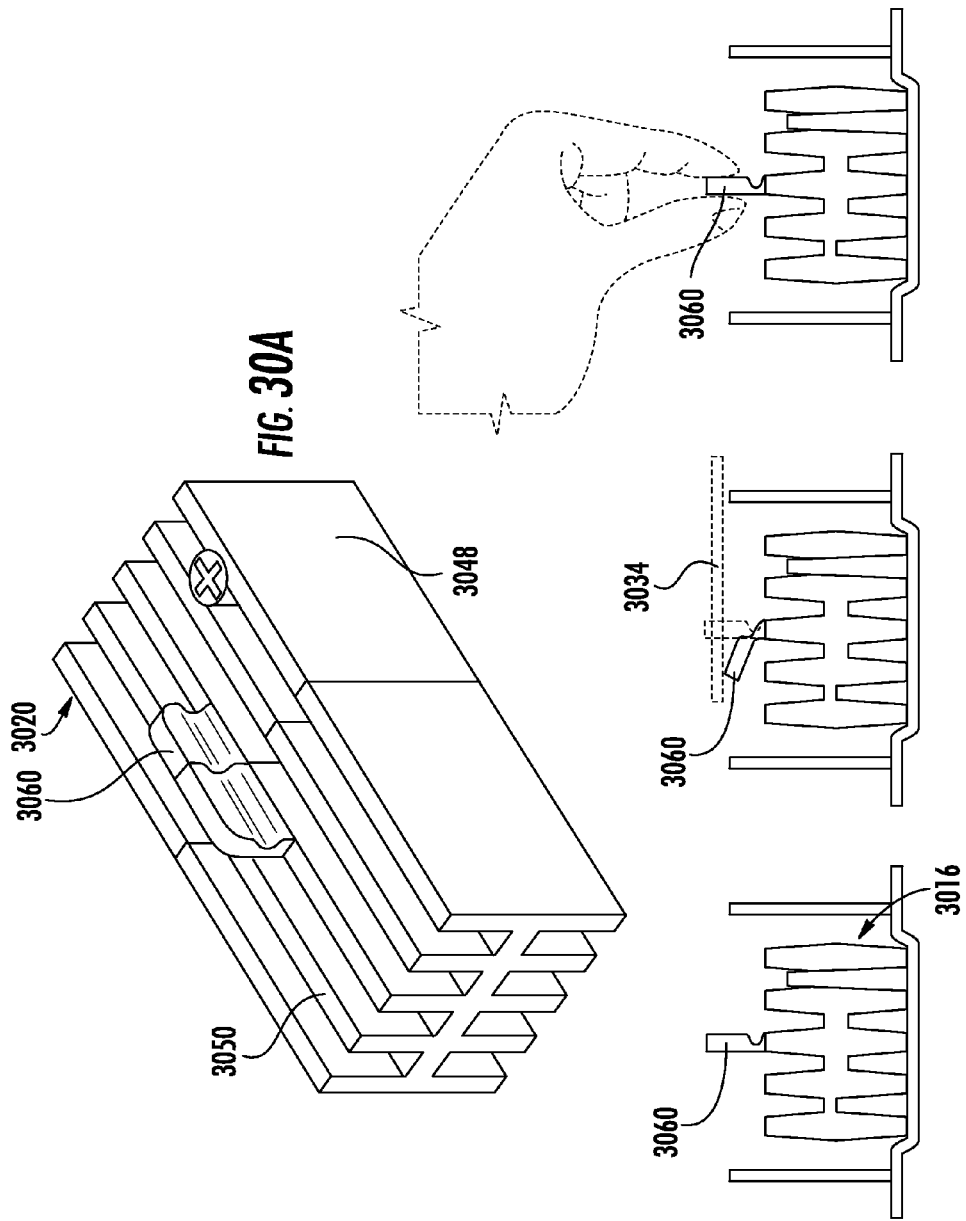

AIR FRESHENER DISPENSERS, CARTRIDGES THEREFOR, SYSTEMS, AND METHODS

CROSS-REFERENCE TO RELATED APPLICATIONS

This application claims priority to U.S. Provisional Application No. 62/030,780, filed Jul. 30, 2014, which is incorporated by reference herein in its entirety.

TECHNICAL FIELD

The present disclosure relates generally to air freshener dispensers and cartridges therefor, and more particularly to air freshener dispensers and cartridges therefor configured for use with paper product and other washroom dispensers.

BACKGROUND

There are numerous problems and frustrations relating to air care and malodor that exist in public washrooms today. To combat malodor, public washroom owners currently rely on a variety of options; however, the current options are expensive, ineffective, or difficult to manage. For example, wall-mounted aerosol systems are the most commonly used option to address malodor. Aerosols often are effective at dispersing fragrance molecules or droplets into a large space quickly, but are messy because a liquid is sprayed into the air. The refill (typically, a canister) is difficult to dispose of, and transportation, packaging, and storage of canisters is a challenge because of their combustion potential. Wall-mounted diffusion (both static and active) systems are new to the public washroom air care space. They are somewhat effective at treating malodor, but refilling them is costly and difficult.

Most public washroom air care solutions are wall-mounted to enable treatment of the entire washroom space with a minimal number of devices. Because the devices are typically mounted high on the wall in order to prevent pilferage and to improve efficacy, they are difficult to access. Also, the fragrance materials in the refills are often liquids, which are messy. Some public washroom owners use retail-like products, such as stand-alone aerosol cans, candles, gels, and diffusers. These are somewhat effective in that they can be used as needed and can be used closer to the source of the malodor, but are very susceptible to pilferage.

Accordingly, there is a need for improved devices and methods to freshen the air and to reduce malodor in public washrooms. Therefore, it is to these ends, as well as other benefits, that the presently disclosed dispensers and cartridges are directed.

SUMMARY

In one aspect, automated air freshener dispensers are provided, including a housing that includes a cavity for receiving a cartridge containing an air freshening substance for release; a fan within the housing that induces an airflow through the housing and directs the airflow to an area outside of the air freshener dispenser, such that released air freshening substance is entrained in the airflow directed from the air freshener dispenser; a motor within the housing for driving the fan; at least one sensor; and a controller within the housing that receives a signal from the at least one sensor and directs operation of the fan in response thereto. In some embodiments, the housing of the air freshener dispenser is mountable to a bath tissue dispenser housing. In some embodiments, the housing of the air freshener dispenser is mountable to another kind of paper product dispenser or to a soap or sanitizer dispenser. In some embodiments, the at least one sensor includes a user-request sensor that senses the hand of a user adjacent the user-request sensor and a second sensor. In some embodiments, the housing includes at least one projection within the cavity, the projection being configured for mating engagement with a recess of the cartridge.

In another aspect, an air freshener cartridge is provided, including a body that includes a polymer impregnated with an air freshening substance selected from an odor-combatting composition, a fragrance, and a combination thereof, wherein the body has a volume of from about 0.1 in$^3$ (1,600 mm$^3$) to about 2.5 in$^3$ (41,000 mm$^3$) and a surface area of from about 2.0 in$^2$ (1,300 mm$^2$) to about 40 in$^2$ (26,000 mm$^2$).

In yet another aspect, an air freshener system is provided, including a cartridge having a body that includes a matrix material impregnated with an air freshening substance for release selected from an odor-combatting composition, a fragrance, and a combination thereof, the body having a volume of from about 0.1 in$^3$ (1,600 mm$^3$) to about 2.5 in$^3$ (41,000 mm$^3$) and a surface area of from about 2.0 in$^2$ (1,300 mm$^2$) to about 40 in$^2$ (26,000 mm$^2$); a housing that includes a cavity containing the cartridge; a fan within the housing that induces an airflow through the housing and directs the airflow to an area outside of the air freshener dispenser, such that released air freshening substance is entrained in the airflow directed from the air freshener dispenser; a motor within the housing for driving the fan; at least one sensor; and a controller within the housing that receives a signal from the at least one sensor and directs operation of the fan in response thereto.

BRIEF DESCRIPTION OF THE DRAWINGS

Referring now to the drawings, which are meant to be exemplary and not limiting, and wherein like elements are numbered alike:

FIG. 14 is a perspective view of a cartridge removal feature.

FIG. 15 is a side view of an air freshener cartridge with flexible engaging features.

FIG. 16 is a side view of a cavity containing an air freshener cartridge and cartridge recognition and depletion sensor associated with the cavity.

FIG. 17 is a side view of a cavity containing an air freshener cartridge with flexible engaging features.

FIG. 18A is a perspective view of an air freshener cartridge.

FIG. 18B is a top view of the cartridge of FIG. 18A.

FIG. 18C is a side view of the cartridge of FIG. 18A.

FIG. 18D is another side view of the cartridge of FIG. 18A.

FIG. 19A is a perspective view of an air freshener cartridge.

FIG. 19B is a top view of the cartridge of FIG. 19A.

FIG. 19C is a side view of the cartridge of FIG. 19A.

FIG. 19D is another side view of the cartridge of FIG. 19A.

FIG. 30A is a perspective view of an air freshener cartridge.

FIG. 30B is a cross-sectional view of the air freshener cartridge of FIG. 30A loaded in a cavity of an air freshener dispenser.

FIG. 30C is a cross-sectional view of the air freshener cartridge of loaded in the cavity of FIG. 30B, with the cavity door closed.

FIG. 30D is a cross-sectional view of a user removing the air freshener cartridge of FIG. 30A from the cavity of FIG. 30B.

DETAILED DESCRIPTION

Disclosed herein are automated air freshener dispensers and cartridges therefor for use with paper product and other washroom dispensers. These dispensers may have one or more of the following benefits over currently available options: (1) improved effectiveness because the dispenser/freshener is closer to the source of the malodor; (2) improved effectiveness because washroom patrons can address instances of acute malodor through on-demand control; (3) easier refillability because the dispenser/freshener is positioned at a lower height than typical wall mounted devices; (4) easier maintenance because the dispenser/freshener does not require a liquid refill; and (5) improved cost effectiveness because the air freshener can be activated only when needed or requested.

Embodiments of the fragrance dispenser systems also solve the problem of combatting malodor without releasing an excessive amount of fragrance, which itself can be perceived as offensive to user and which can deplete the cartridge unnecessarily rapidly. As described herein, the problem is solved by a combination of the freshener cartridge configuration, cavity configuration, and fan configuration to achieve a desirable quantity and rate of release of the fragrance. Effective configurations were developed from testing.

Air Freshener Dispensers

Automated air freshener dispensers are provided herein. In certain embodiments, the automated air freshener dispensers are configured to be integrated with or onto a paper product dispenser, such as a bath tissue dispenser. As used herein, the terms "air freshener" and "air freshening" refer to substances that treat air by combatting or neutralizing odor, providing a fragrance, or both.

Figure 1A:
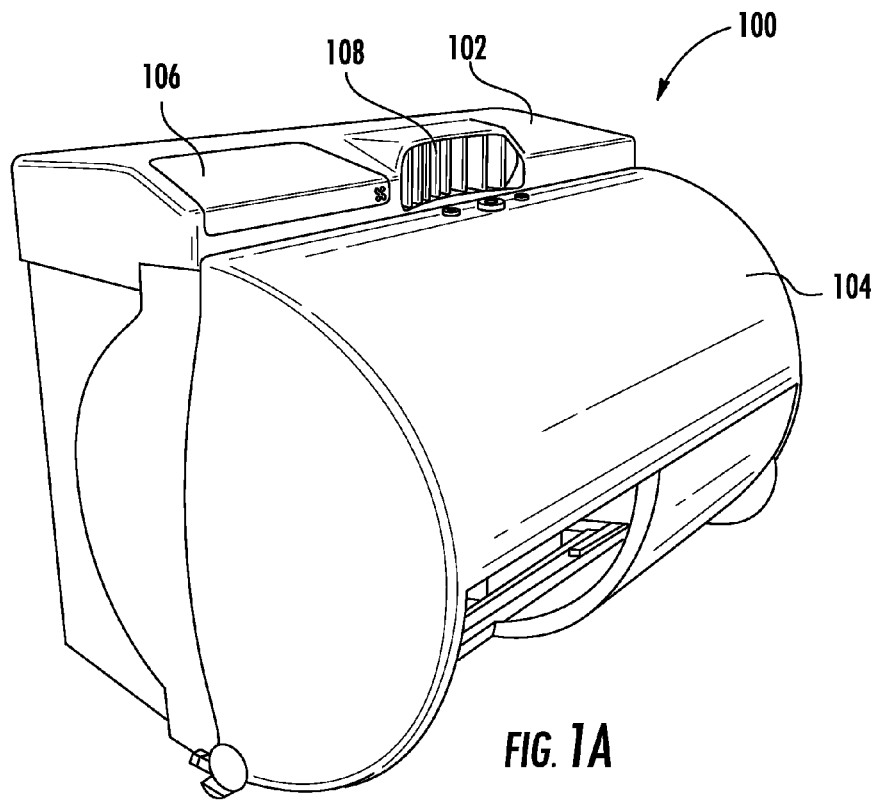
FIG. 1A is a perspective view of a combined air freshener and paper product dispenser.
Figure 1B:
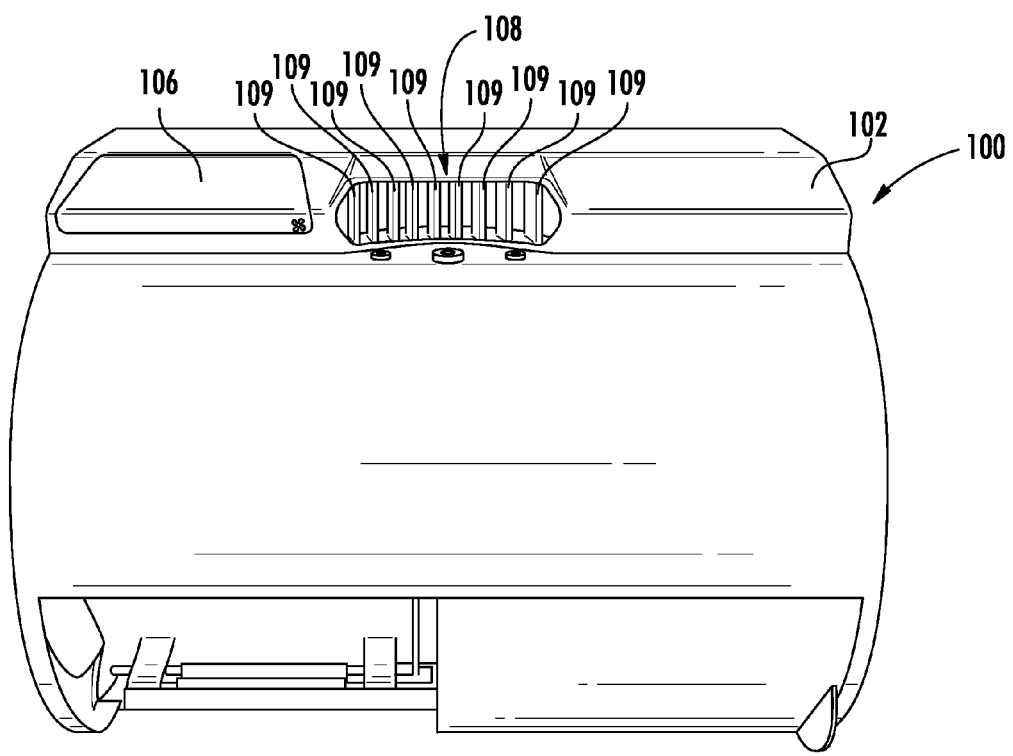
FIG. 1B is a front perspective view of the combined air freshener and paper product dispenser of FIG. 1A.

In certain embodiments, as shown in FIGS. 1A and 1B, the housing 103 of an automated air freshener dispenser 102 is mountable to a bath tissue dispenser housing 104 to form a combined air freshener and paper product dispenser 100. As used herein, the phrase "mountable to a bath tissue dispenser housing" refers to the housing of the automated air freshener dispenser being configured for attachment or coupling to the housing of a bath tissue dispenser. For example, the housing of the air freshener dispenser may be configured for attachment to the housing of a bath tissue dispenser by adhesives, solder, welding, magnetic connection, hook-and-loop fasteners, mechanical fasteners, such as screws or bolts, or corresponding snap fit features in the housings.

Figure 5:
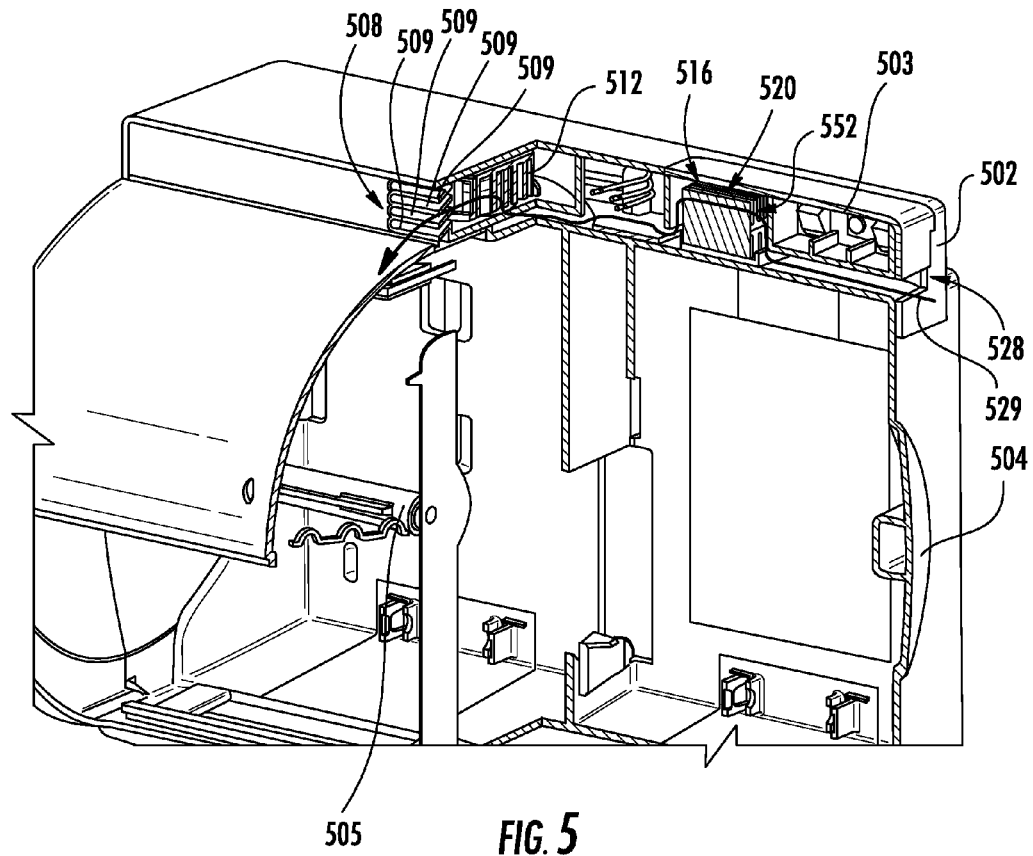
FIG. 5 is a partial cross-sectional perspective view of a combined air freshener and paper product dispenser.

In one embodiment, the housing 103 of the air freshener dispenser 102 is configured to be snap fit to the bath tissue dispenser housing 104. For example, as shown in FIG. 5, a bath tissue dispenser may include a bath tissue dispenser housing 504 having a discharge opening for dispensing bath tissue therethrough and a spindle 505 disposed within the housing 504 for supporting a roll of the bath tissue.

Thus, in some embodiments, the air freshener dispenser is a self-contained module that is adaptable to fit onto or to be integrated with an existing paper product dispenser (i.e., is retrofittable onto an existing paper product dispenser). In other embodiments, the air freshener dispenser is integrally formed with a paper product dispenser.

While embodiments of the present air freshener dispensers are generally described as being configured for integration with manual bath tissue dispensers, it should be understood that the air freshener dispensers described herein may be combined with any suitable dispensers, such as other automated and manual paper product dispensers (e.g., bath tissue and paper towel dispensers), and soap or sanitizer dispensers, among others. In one embodiment, the housing of the air freshener dispenser is mountable to a paper product dispenser or a soap or sanitizer dispenser.

Figure 2:
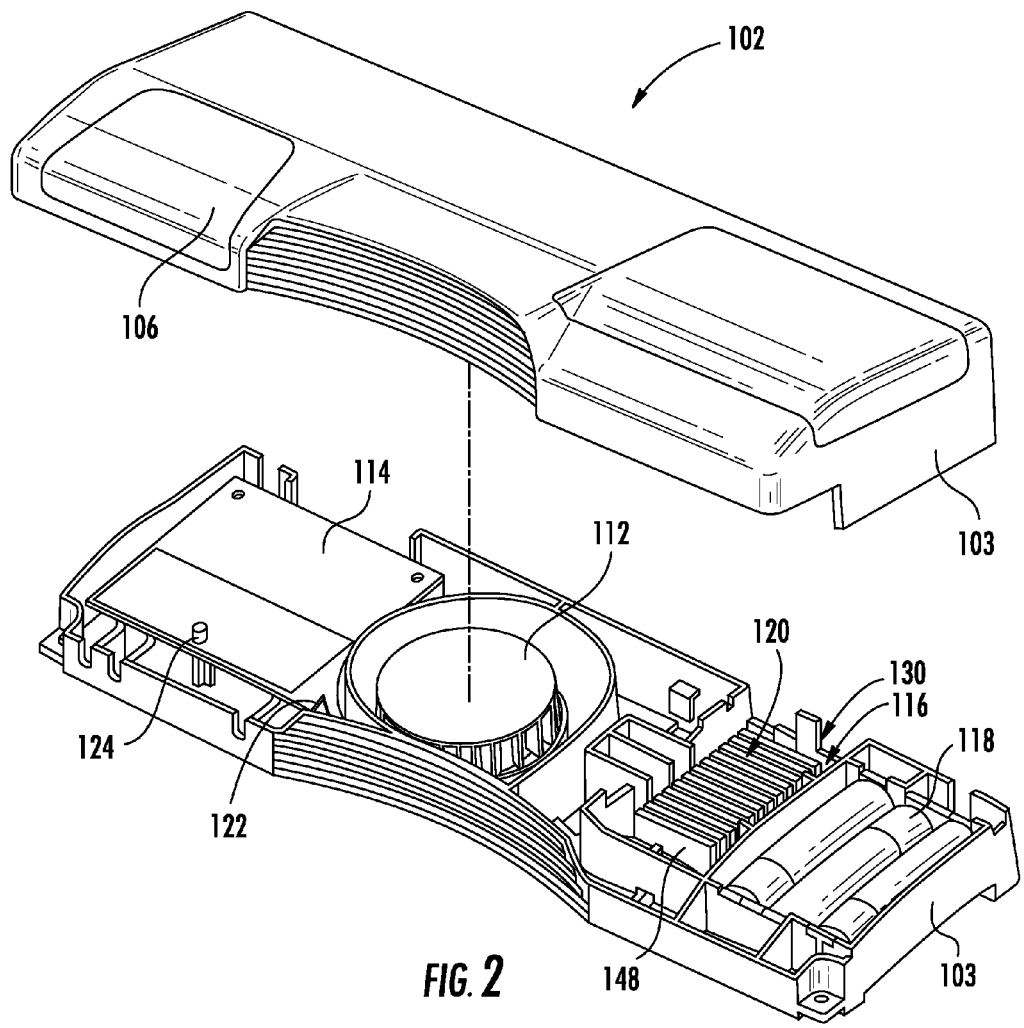
FIG. 2 is an exploded perspective view of an automated air freshener dispenser.
Figure 3:
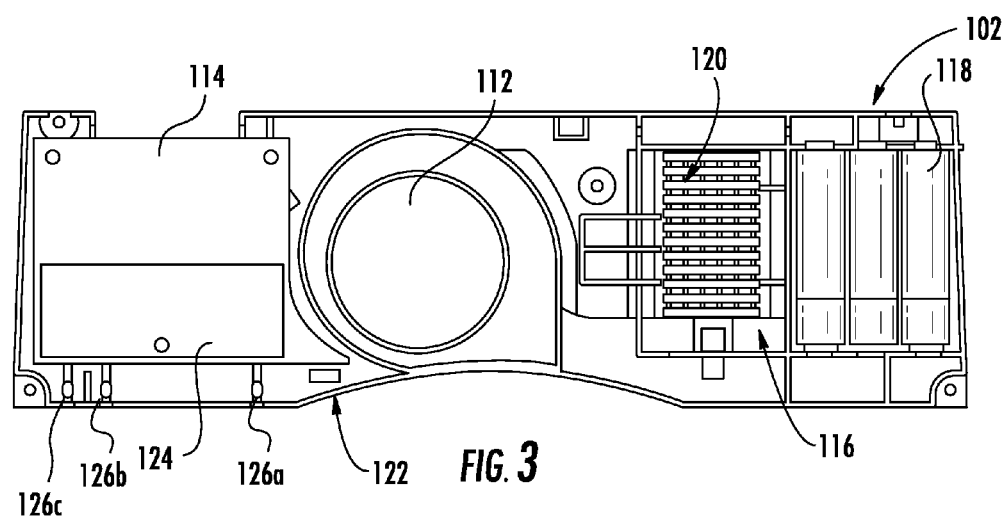
FIG. 3 is a top plan view of the interior of an automated air freshener dispenser.

In certain example embodiments, as shown in FIGS. 2 and 3, an automated air freshener dispenser 102 includes a housing 103 that includes a cavity 116 for receiving a cartridge 120 containing an air freshening substance for release. Various cartridge designs are described herein; however, the air freshener dispensers described herein are not limited to use with such cartridges. Instead, the air freshener dispenser described herein may be used with any suitable cartridges known in the art. As used herein, the term "cartridge" or "air freshener cartridge" refers to a self-supporting solid substance containing an air freshening substance, or a semi-solid substance containing an air freshening substance and that is supported by a container, and assemblies containing such substances, that are configured to release the air freshening substance by volatilization and diffusion-based release thereof. For example, cartridges for use with the presently described air freshener dispensers may have any suitable composition, size, and shape to fit within the dispenser such that the desired rate and intensity of release of the air freshening substance is achieved.

In some embodiments, the housing includes a transparent window over the cavity, such that maintenance personnel can see the cartridge depletion level through the window. In certain embodiments, the cavity for receiving the cartridge is removable, such that the cavity geometry may be customized based on the desired air freshener release profile and particular cartridge geometry. In certain embodiments, the housing includes more than one cavity for receiving a cartridge and/or the cavity is configured to receive more than one cartridge, such that cartridges having different air freshening properties (e.g., difference fragrances) may be housed in a single dispenser.

The automated air freshener dispenser 102 also includes a fan 112 within the housing 103 that induces an airflow through the housing 103 and directs the airflow to an area outside of the air freshener dispenser 102, such that released air freshening substance is entrained in the airflow directed from the air freshener dispenser 102. The automated air freshener also includes a motor (not shown) within the housing 103 for driving the fan 112, at least one sensor 122, 124, and a controller 114 within the housing 103 that receives a signal from the at least one sensor 122, 124 and directs operation of the fan 112 in response thereto. For example, the controller 114 may be any suitable controller, such as a circuit board, microchip, or electronic or mechanical control device, as are known in the art. As will be described in more detail herein, the controller provides logic and control functionality used during operation of the air freshener dispenser. Alternatively, the functionality of the controller may be distributed to several controllers that each provides more limited functionality to discrete portions of the operation of the air freshener dispenser. In some embodiments, the air freshener dispenser 102 also includes a power source, such as one or more batteries 118, a hard wired electrical connection, solar panel(s), or other suitable power sources known in the art, to power the components of the dispenser 102.

Thus, the fan 112 may be run in response to receipt of a signal by the sensor(s) 122, 124, to release the air freshening substance to the air space adjacent the dispenser 102. For example, the air freshening dispenser 102 may be provided in a washroom stall, such as mounted on the bath tissue dispenser 104. The sensor(s) may include user-request and/or user-presence sensors. As used herein, the term "user-request sensor" refers to any suitable sensor that can detect a user waving a hand near the dispenser, such as a motion or proximity sensor. As used herein, the term "user-presence sensor" refers to any suitable sensor that can detect a user's presence within a certain range of the sensor. For example, as user-presence sensor may be configured to detect the presence of a user in a washroom stall or at the toilet within the stall.

In embodiments of the air freshener dispenser for use in a washroom stall, the sensor(s) 122, 124 may be selected from a variety of suitable sensors, including, but not limited to, motion sensors, proximity sensors, light sensors, odor sensors, thermal sensors, and switches. For example, a motion sensor may be configured to sense short or long distance motion within a washroom stall, such as a user opening the door and entering the stall or a user waving a hand near the dispenser (i.e., a user request for dispense). For example, a switch may be configured to sense the opening or closing of a washroom stall door or the presence or absence of a user at the toilet within the stall. Thus, the air freshener dispenser 102 may be configured to release the air freshening substance in a variety of circumstances, depending on the location of the dispenser and the desired air freshener release parameters. In certain embodiments, the freshener dispenser 102 may be configured to release the air freshening substance independently of the withdrawal by a user of tissue from a bath tissue dispenser associated with the air freshener dispenser. Hence, a user of a washroom advantageously does not have to touch any surface of the dispenser, or touch and manually activate an aerosol fragrance spray, for instance, in order to release fragrance or reduce malodor.

As shown in FIG. 5, the air freshener dispenser housing 503 includes an air inlet 528 and an airflow outlet 508, through which the airflow containing the entrained released air freshening substance is directed from the dispenser 502 at least partially via actuation of the fan 512. An airflow path 529 from the air inlet 528 to the airflow outlet 508 may be defined within the housing. In certain embodiments, the airflow path 529 includes airflow through and/or around the air freshener cartridge 520 within the cavity 516, so as to volatilize the air freshening substance present at one or more surfaces of the cartridge and entrain the air freshening substance in the airflow. For example, illustrations of airflow through and around various air freshener cartridges are provided at FIGS. 18E, 18F, 19E, 19F, 20E, and 20F. For ease of illustration, these figures show the airflow through and around the cartridges separately; however, it should be understood that in typical operation, airflow both around and through the cartridge will occur simultaneously.

In certain embodiments, the airflow path 529 from the air inlet 528 to the airflow outlet 508 is tortuous. As used herein, the term "tortuous" refers to the airflow path having a non-linear course through the housing. For example, a tortuous airflow path 529 may reduce the passive release of air containing entrained released air freshening substance through the airflow outlet. As used herein, the terms "passive release of air containing entrained released air freshening substance" and "passively released air freshening substance" refer to release of the air freshening substance from the cartridge absent actuation of the fan.

In certain embodiments, as shown in FIG. 5, the housing 503 of the air freshener dispenser 502 is designed to have a particular total headspace volume and/or to have a particular cavity headspace volume. As used herein, the term "headspace" refers to the unoccupied volume of the specified compartment. For example, the term "cavity headspace" refers to the air space volume of the empty cavity (i.e., prior to loading of a cartridge therein) that is not occupied by structural features of the cavity (e.g., projections from the cavity base or cover, cartridge removal features). Thus, when a cartridge is loaded in the cavity, the headspace within the cavity will be reduced by the volume of the cartridge. For example, the term "housing headspace" refers to the air space volume within the housing not occupied by the various components contained within the housing (e.g., controller, fan, motor, power source). For example, the headspace volume of the housing and/or cavity may be selected to accommodate a certain volume of air containing entrained passively released air freshening substance, such as the air containing entrained passively released air freshening substance that accumulates between actuation cycles of the fan. In some embodiments, the housing has a headspace volume of from about 15 in$^3$ (250,000 mm$^3$) to about 45 in$^3$ (740,000 mm$^3$), of from about 25 in$^3$ (410,000 mm$^3$) to about 35 in$^3$ (570,000 mm$^3$), or of about 30 in$^3$ (490,000 mm$^3$). In certain embodiments, the cavity has a headspace volume of from about 0.2 in$^3$ (3,300 mm$^3$) to about 4 in$^3$ (70,000 mm$^3$). In some embodiments, the cavity has a headspace volume of from about 1 in$^3$ (20,000 mm$^3$) to about 4 in$^3$ (70,000 mm$^3$), of from about 2 in$^3$ (30,000 mm$^3$) to about 3 in$^3$ (50,000 mm$^3$), or of about 2.5 in$^3$ (40,000 mm$^3$). As used herein, the term "about" means plus or minus 10 percent of the numerical value of the number with which it is being used.

In certain embodiments, the fan 512 is configured to pull and/or push any air containing entrained passively released air freshening substance that accumulates between actuation cycles of the fan and to induce airflow through and/or around the air freshener cartridge 520 within the cavity 516, so as to volatilize the air freshening substance present at one or more surfaces of the cartridge and entrain the air freshening substance in the airflow. Thus, the fan 512 may be configured to induce airflow through the housing 503 and to direct airflow of any accumulated air containing entrained passively released air freshening substance in the housing 503 and/or cavity 516 headspaces, as well as airflow containing entrained released air freshening substance induced by actuation of the fan 512, to be released from the dispenser 502. In certain embodiments, as shown in FIG. 5, the fan 512 is positioned within the housing 503 between the airflow outlet 508 and the cavity 516. In such embodiments, the fan 512 pulls airflow through and/or around a cartridge 520 contained in the cavity 516. In other embodiments, the cavity is positioned between the airflow outlet and the fan, such that the fan pushes airflow through and/or around a cartridge contained in the cavity.

As discussed in more detail below, the cartridge may have airflow channels that are configured to align with the airflow path when the cartridge is loaded in the cavity, to maximize airflow through the air freshener cartridge and to increase the exposed surface area of the cartridge from which air freshening substance may be volatilized, thereby appropriately maximizing release of the air freshening substance.

In some embodiments, as shown in FIG. 2, the fan 112 is a centrifugal fan or an axial fan. In certain embodiments, the fan has a speed of from about 500 rpm to about 4000 rpm. In some embodiments, the fan has a speed of from about 1,000 rpm to about 2,000 rpm. For example, the fan may have a speed of about 1,800 rpm. The fan may be controlled to operate for a set time period once the sensor has been triggered, such as from 5 to 120 seconds, from 5 to 60 seconds, or from 10 to 45 seconds, and the like. As is described in more detail below, the controller also can be programmed with a time delay, which can be adjusted, between periods of fan rotation (operation). As an example, the controller can prevent continuous fan rotation by implementing a time delay of from 5 seconds to 10 minutes, from 5 to 60 seconds, or from 10 to 45 seconds, between periods of fan rotation.

In certain embodiments, the fan 112 is configured such that the airflow containing the entrained released air freshening substance is directed from the air freshener dispenser 103 at a volume of from about 0.1 ft$^3$/min (0.003 m$^3$/min) to about 10 ft$^3$/min (0.3 m$^3$/min). In some embodiments, the fan 112 is configured such that the airflow containing the entrained released air freshening substance is directed from the air freshener dispenser 102 at a volume of from about 0.5 ft$^3$/min (0.01 m$^3$/min) to about 5 ft$^3$/min (0.14 m$^3$/min). In some embodiments, the fan 112 is configured such that the airflow containing the entrained released air freshening substance is directed from the air freshener dispenser 102 at a volume of from about 1 ft$^3$/min (0.03 m$^3$/min) to about 3 ft$^3$/min (0.09 m$^3$/min). For example, the fan 112 may be configured such that the airflow containing the entrained released air freshening substance is directed from the air freshener dispenser 102 at a volume of about 1.1 ft$^3$/min (0.031 m$^3$/min), about 1.4 ft$^3$/min (0.040 m$^3$/min), or about 1.9 ft$^3$/min (0.054 m$^3$/min).

Thus, an air freshener dispenser 102 may be designed to provide a desired release of air freshening substance by selecting particular dispenser housing 103 and cavity 116 sizes, as well as fan 112 parameters (e.g., volumetric air release rate), for a cartridge 120 having a particular geometry (e.g., volume, surface area) and composition (e.g., air freshening substance loading).

As discussed above, air containing air freshening substance passively released from the cartridge may flow from the housing with or without actuation of the fan. When the fan is stationary, air containing air freshening substance passively released from the cartridge may flow from the airflow outlet and/or from an air vent in the housing. In some embodiments, as shown in FIG. 2, the housing 103 includes a vent 130 for allowing passive airflow from the air freshener dispenser therethrough. The vent may be distinct from the airflow outlet of the dispenser and may be disposed on a face of the dispenser housing other than the face in which the airflow outlet is disposed. For example, the vent may be disposed in a rear face of the dispenser housing (i.e., the face of the housing that faces the wall on which the dispenser is mounted), such that the vent is not generally accessible. In some embodiments, the vent has an open area of from about 0.1 $in^2$ (60 $mm^2$) to about 10 $in^2$ (6,000 $mm^2$). In some embodiments, the vent has an open area of from about 0.1 $in^2$ (60 $mm^2$) to about 5 $in^2$ (3,000 $mm^2$). For example, the vent may have an open area of about 0.6 $in^2$ (400 $mm^2$). In some embodiments, the housing further includes a mechanism to restrict flow of the air containing air freshening substance passively released from the cartridge. For example, the housing may include a valve, such as a one-way flow valve, that permits airflow therethrough only when the air pressure at the valve reaches a threshold pressure.

Figure 6:
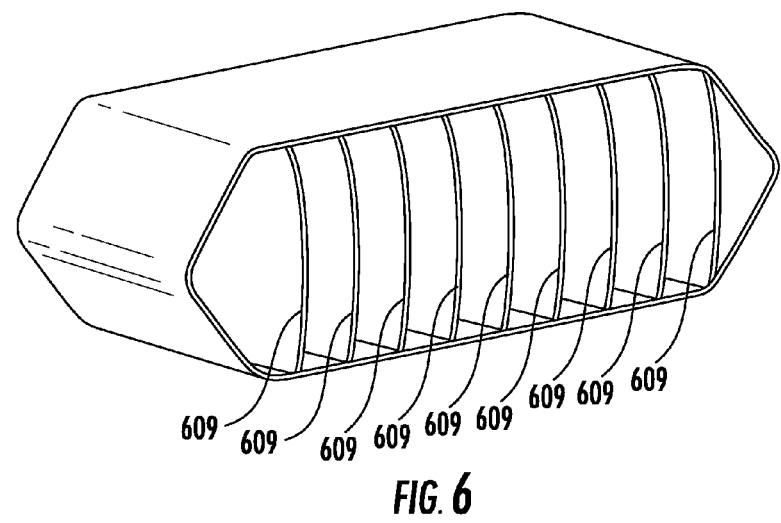
FIG. 6 is a perspective view of a detachable louver assembly for an airflow outlet of an air freshener dispenser.

In certain embodiments, as shown in FIG. 5, the airflow outlet 508 includes at least one louver 509 to direct the airflow direction out of the air freshener dispenser 502. In one embodiment, as shown in FIG. 5, the at least one louver 509 is configured to direct the airflow downward. In another embodiment, as shown in FIGS. 1A and 1B, wherein the at least one louver 109 of the airflow outlet 108 is configured to direct the airflow at an angle from between 0 degrees and 80 degrees relative to a face of the housing in which the airflow outlet is located. In other embodiments, the louver of the airflow outlet is configured to direct the airflow at an angle from between 10 degrees and 170 degrees relative to a face of the housing in which the airflow outlet is located. For example, the louvers may be configured to direct the airflow away from an occupant of the stall, such as by directing the airflow upwards, downwards, or laterally toward the sides of the dispenser. In certain embodiments, as shown in FIG. 6, the louver(s) 609 are detachably associated with the housing of the dispenser. That is, the louver(s) can be removed and reattached in a different orientation, e.g., by snap-fit engagement. Such detachable louver(s) may allow the louver(s) to be selectively positioned (e.g., inverted) to direct airflow away from a washroom stall occupant, depending on the placement of the dispenser in the stall. In certain embodiments, the airflow outlet includes a shuttering mechanism or adjustable louver(s) to adjust the direction and/or volume of airflow out of the airflow outlet.

Figure 4:
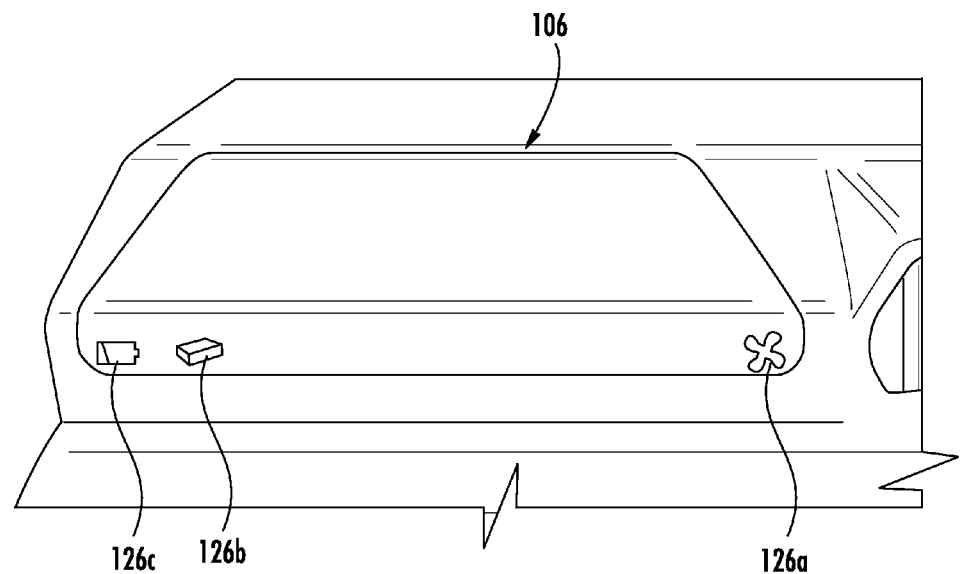
FIG. 4 is a perspective view of a status indicator panel of an air freshener dispenser.

In certain embodiments, as shown in FIGS. 1A and 1B, the air freshener dispenser 102 also includes at least one status indicator 106 indicating some status information about the dispenser or its components. For example, as shown in FIGS. 3 and 4, the status indicator 106 may include lights that indicate a cartridge depletion status 126*b* (e.g., indicating that the air freshener cartridge is spent or near spent and needs to be replaced), a fan operation status 126*a* (e.g., indicating that the fan is running), a power source status 126*c* (e.g., indicating that the batteries are low on power and need to be replaced), or any combination thereof. Additionally, the status indicator may indicate information regarding the level of air freshening (e.g., fragrance and/or odor control) provided by the dispenser, such as a meter showing the relative amount of air freshener being released when the dispenser is operated. In some embodiments, the status indicator indicates that it senses a user presence and/or a user request for dispense of air freshening substance. For example, the status indicator lights may be LED or other suitable lights. At times when these events are not occurring, the status indicator lights can be dark (i.e., not lit). The status information and the status indicators can be monitored and/or controlled by the controller. Thus, in certain embodiments, the controller receives information regarding the cartridge depletion status, the fan operation status, or the power source status and instructs activation of a corresponding status indicator light in response thereto.

Status information about the dispenser and/or its components may be determined via a variety of suitable means. For example, the cartridge depletion status information may be determined and provided to the controller by a sensor, a timer, or both. For example, a mechanical cartridge depletion sensor may be configured to sense changes in the presence of, mass, or dimensions of the cartridge. For example, the sensor may include a load cell, a mechanically actuated switch, or a proximity sensor. In certain embodiments, as shown in FIG. 16, the housing of the dispenser may include a switch 1546 in communication with the cavity 1516 such that when a new cartridge 1520 is introduced into the cavity 1516, the switch is engaged by a portion 1542 of the cartridge 1520. In these embodiments, when the cartridge depletes to a certain extent or is removed, the switch is disengaged. Other means to determine cartridge introduction into the cavity include an RFID reader in the housing for reading an RFID tag associated with the cartridge. In certain embodiments, a sensor is configured to detect introduction of a cartridge into the cavity and to initiate a timer in response thereto, such that the timer indicates cartridge depletion after a certain period of time (e.g., 30, 60, or 90 days). Alternatively, the sensor may be configured to detect depletion of the cartridge, such that a cartridge depletion signal is transmitted to the controller upon the sensor sensing a certain level of depletion. For example, depletion may be determined by a pre-selected reduction in a dimension, which may be optically or mechanically detected, or by a pre-selected reduction in weight of the cartridge, which may be detected by a load cell.

In certain embodiments, the housing includes a user interface that accepts user input (e.g., via buttons) on various dispenser features. For example, the user interface may allow a user to select a particular fragrance for dispense or a level (correlated to quantity) of air freshener released by the dispenser, among other dispenser parameters. In one embodiment, the user interface allows the user to close or partially close the airflow outlet, such as by shuttering it, or to adjust the direction or angle of airflow out of the airflow outlet, such as by adjusting the louver(s).

In certain embodiments, the air freshener dispenser further includes dispenser usage information tracking and other metric tracking capabilities. For example, the air freshener dispenser may include one or more sensors configured to track dispenser usage, throughput, number of people using the dispenser, off/on signals, battery, breakage, cartridge depletion, and introduction and authenticity of a cartridge into the cavity, among others. In some embodiments, a Bluetooth or other communication device in communication with the controller of the air freshener dispenser communicates dispenser status information and/or metrics to a network hub for monitoring.

Figure 13:
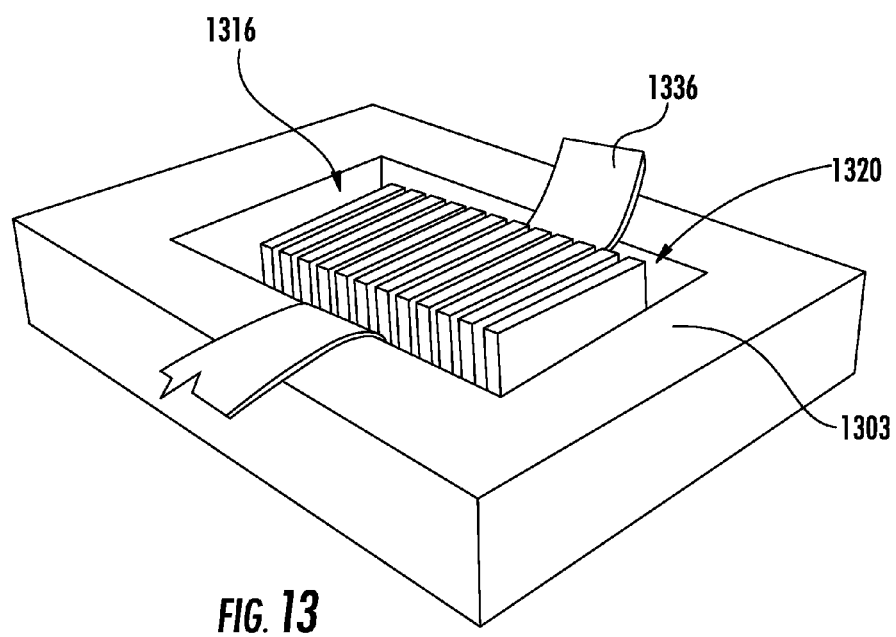
FIG. 13 is a perspective view of cavity having a cartridge removal feature.
Figure 18E:
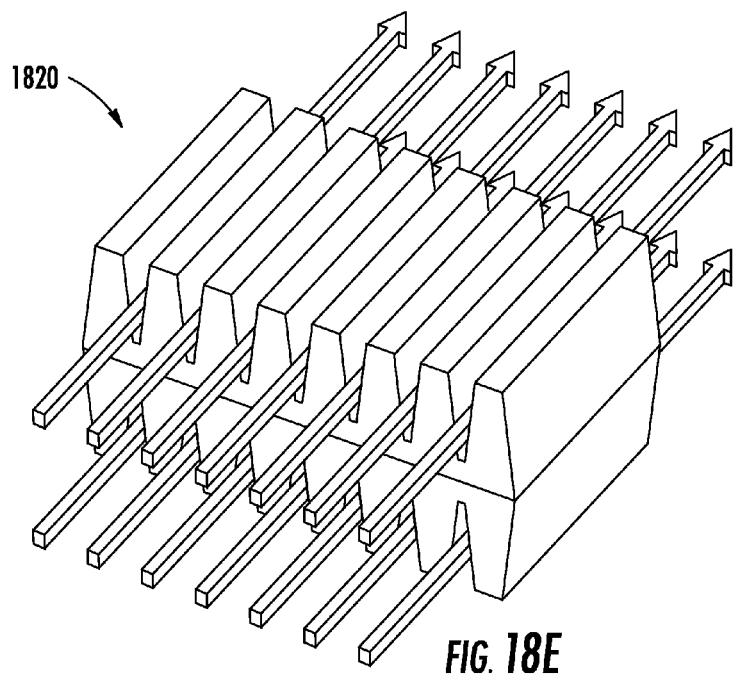
FIG. 18E a perspective view showing airflow through the cartridge of FIG. 18A.
Figure 18F:
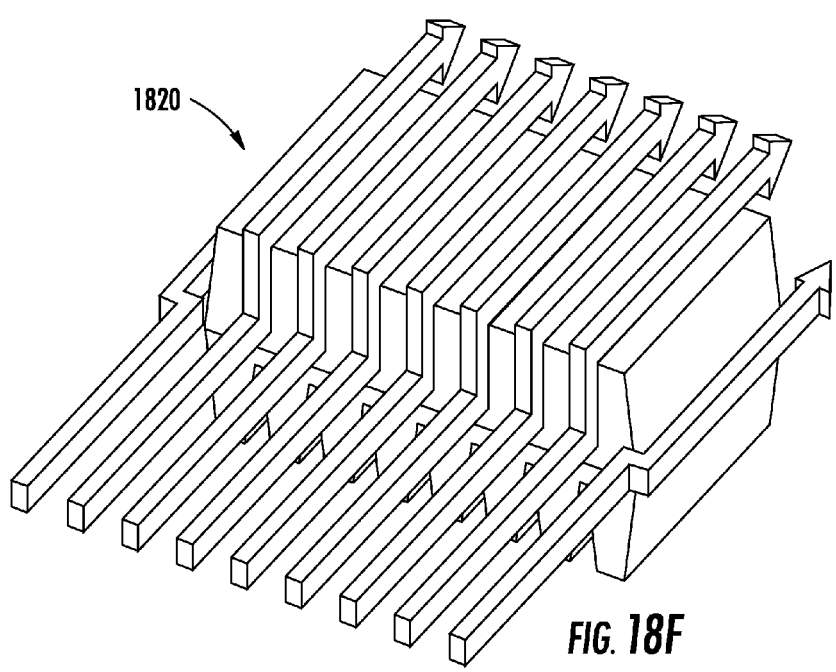
FIG. 18F is a perspective view showing airflow around the cartridge of FIG. 18A.
Figure 19E:
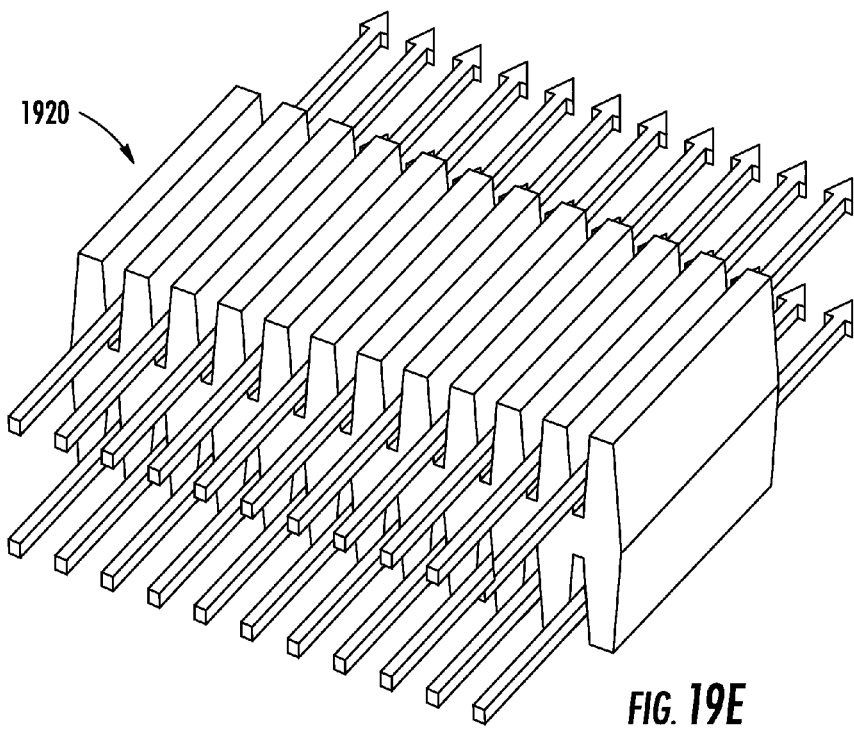
FIG. 19E a perspective view showing airflow through the cartridge of FIG. 19A.
Figure 19F:
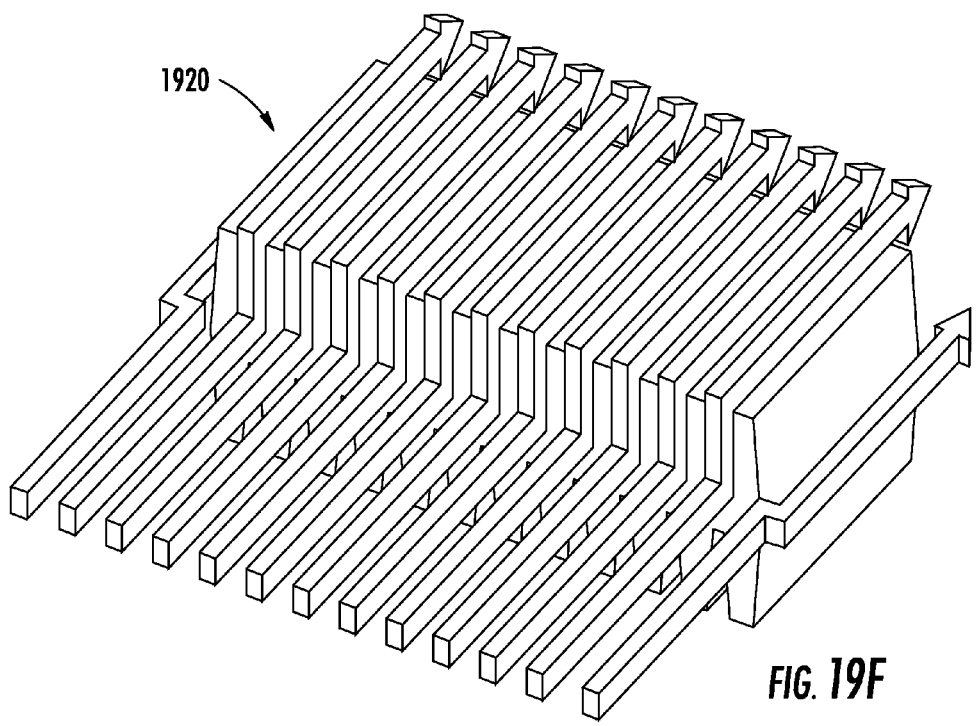
FIG. 19F is a perspective view showing airflow around the cartridge of FIG. 19A.

In certain embodiments, as shown in FIGS. 13 and 14, the housing includes a cartridge removal feature for aiding in removal of a depleted cartridge from the cavity by maintenance personnel. For example, as shown in FIG. 13, the housing 1303 may include a ribbon or flexible strip 1336 that is partially disposed in the cavity 1316 under a cartridge 1320 loaded therein, such that an end of the flexible strip 1336 is outside of the cavity 1316 when a cartridge 1320 is loaded therein to allow for removal of the cartridge 1320 from the cavity 1316 by pulling on the exposed end of the flexible strip 1336. In another embodiment, as shown in FIG. 14, the cavity contains a spring loaded plate 1438 onto which the cartridge may be loaded, such that the cartridge is partially outside the cavity, and thereby accessible, when the spring is disengaged. In one embodiment, a spring is associated with the cavity such that when the spring is engaged, the refill sits completely within the cavity, and, when the spring is disengaged, the refill sits partially outside the cavity, making it accessible to a user for removal. For example, the spring may be disposed such that it contacts the cartridge within the cavity, such that a user may push on the cartridge to engage or disengage the spring.

As discussed above, in embodiments of the present disclosure, automated air freshener dispensers include at least one suitable sensor and a controller that is configured to receive a signal from the at least one sensor and directs operation of the fan in response thereto. In certain embodiments, as shown in FIG. 3, an automated air freshener dispenser 102 includes a user-request sensor 124 that senses the hand of a user adjacent the user-request sensor 124 and a second sensor 122. In these embodiments, the controller 114 is configured to receive signals from the user-request sensor and the second sensor and to direct operation of the fan in response thereto. In certain embodiments, the second sensor is a user-presence sensor, such as a motion sensor, proximity sensor, light sensor, odor sensor (e.g., sensing malodor or fragrance), or switch. For example, the second sensor may be configured to sense the presence of a user in an area near the dispenser (e.g., in the washroom stall in which the air freshener dispenser is located), independent of a user-request. For example, a motion sensor may be configured to sense motion within a washroom stall, such as a user opening the door and entering the stall. For example, a switch may be configured to sense the opening or closing of a washroom stall door or the presence or absence of a user at the toilet within the stall, such as via a pressure sensor at the seat of the toiler. In some embodiments, the sensor(s) is configured to sense the rotation or dispense of bath tissue, other paper products, soap, sanitizer, or another product from an associated product dispenser. For example, the sensor(s) may be configured to sense the manual dispense of bath tissue from an associated bath tissue dispenser, such as by sensing rotation of a spindle of the bath tissue dispenser. In some embodiments, the sensor(s) is configured to sense the flushing of a toilet within the washroom stall or another event.

In one embodiment, as shown in FIG. 3, an air freshener dispenser 102 includes a user-request sensor 124 and a user-presence sensor 122, such as a motion sensor or any other user-presence sensors described herein, for sensing the presence of a user in the washroom stall. In some embodiments, the user-request sensor is a short range sensor and the motion sensor is a longer range sensor. For example, the short and long range sensors may both be passive infrared sensors. In some embodiments, the user-request sensor is a capacitive sensor.

In certain embodiments, an automated air freshener dispenser includes a user-presence sensor that senses the presence of a user within a certain space or location and a second sensor. In these embodiments, the second sensor may be a user-request sensor that senses the hand of a user adjacent the user-request sensor.

As discussed above, the controller may be configured to direct the motor to drive the fan for a predetermined duration in response to receipt of a signal from the sensor(s). For example, the predetermined duration may be from about 5 seconds to about 60 seconds, from about 10 to about 45 seconds, from about 25 seconds to about 35 seconds, or about 30 seconds. In certain embodiments, the controller is further configured to prevent the fan from operating if the fan was run recently, even if the sensor(s) has been activated. This feature advantageously can mitigate over-release of fragrance and abuse of the dispenser. In one embodiment, the controller is configured to determine whether the fan has been driven within a predetermined period preceding receipt of a signal from the at least one sensor and to prevent the motor from driving the fan in response to receipt of the signal if the fan has been driven within the predetermined period preceding receipt of the signal. For example, the predetermined period is from about 5 seconds to about 10 minutes, from about 10 seconds to about 45 seconds, or from about 20 to about 30 seconds. In other embodiments, the controller is not configured to prevent the motor from driving the fan upon receipt of a signal from the at least one sensor.

Thus, the controller may be configured to have a certain logic sequence that controls the running (or preventing the running) of the fan in response to signals from the sensor(s), and the period the fan runs in response to receipt of signals from the sensor(s). In certain embodiments, the controller directs the motor to drive the fan for a first duration in response to receipt of a signal from a first sensor and to drive the fan for a second duration that is shorter or longer than the first duration in response to receipt of a signal from a second sensor. For example, the controller may be configured to direct running of the fan for a longer duration upon receipt of a signal from the motion sensor and for a shorter duration upon receipt of a signal from a user-request sensor. In other embodiments, the controller directed the motor to drive the fan for a certain duration upon receipt of a signal from any of the sensor(s) of the dispenser.

In certain embodiments in which the dispenser includes a user-request sensor and a second sensor, the air freshener dispense cycle begins with one activation of the second sensor and may include multiple user-request activations. That is, after an initial detection of motion or another event (e.g., an occupant entering a stall, the stall door closing, a user near or on the toilet within the stall), the air freshener dispenser runs the fan for a first duration, for example from 20 to 50 seconds. After this initial detection of a non-user-request event by the second sensor, the logic may prevent the running of the fan in response to a signal from the second sensor for a period of time, for example from 2 to 6 minutes. Thus, after the initial activation of the fan in response to the signal from the second sensor, the controller may run the fan only in response to receipt of a signal from the user-request sensor within the 2 to 6 minute period. In response to a signal from the user-request sensor, the controller may direct running of the fan for a second duration, for example from 10 to 30 seconds. In some embodiments, the controller logic prevents the running of the fan in response to a signal from the second sensor for the period of time, for example from 2 to 6 minutes, after the running of the fan in response to any signal type. In some embodiments, the controller further prevents running of the fan in response to a signal from the user-request sensor for a period of time, for example, 10 to 40 seconds, after the running of the fan in response to any signal type.

In some embodiments, the controller is configured (i) to direct the motor to drive the fan for a duration from about 20 seconds to about 50 seconds in response to receipt of a signal from the motion sensor, (ii) to direct the motor to drive the fan for a duration from about 10 seconds to about 30 seconds in response to receipt of a signal from the user-request sensor, and (iii) to determine whether the fan has been driven within a period of from about 10 to about 40 seconds preceding receipt of a signal from the user-request sensor and to prevent the motor from driving the fan in response to receipt of the signal from the user-request sensor if the fan has been driven within the period preceding receipt of the signal. In certain embodiments, the controller is further configured to determine whether the fan has been driven within a period of from about 2 minutes to about 6 minutes preceding receipt of a signal from the motion sensor and to prevent the motor from driving the fan in response to receipt of the signal from the motion sensor if the fan has been driven within the period preceding receipt of the signal.

Figure 43:
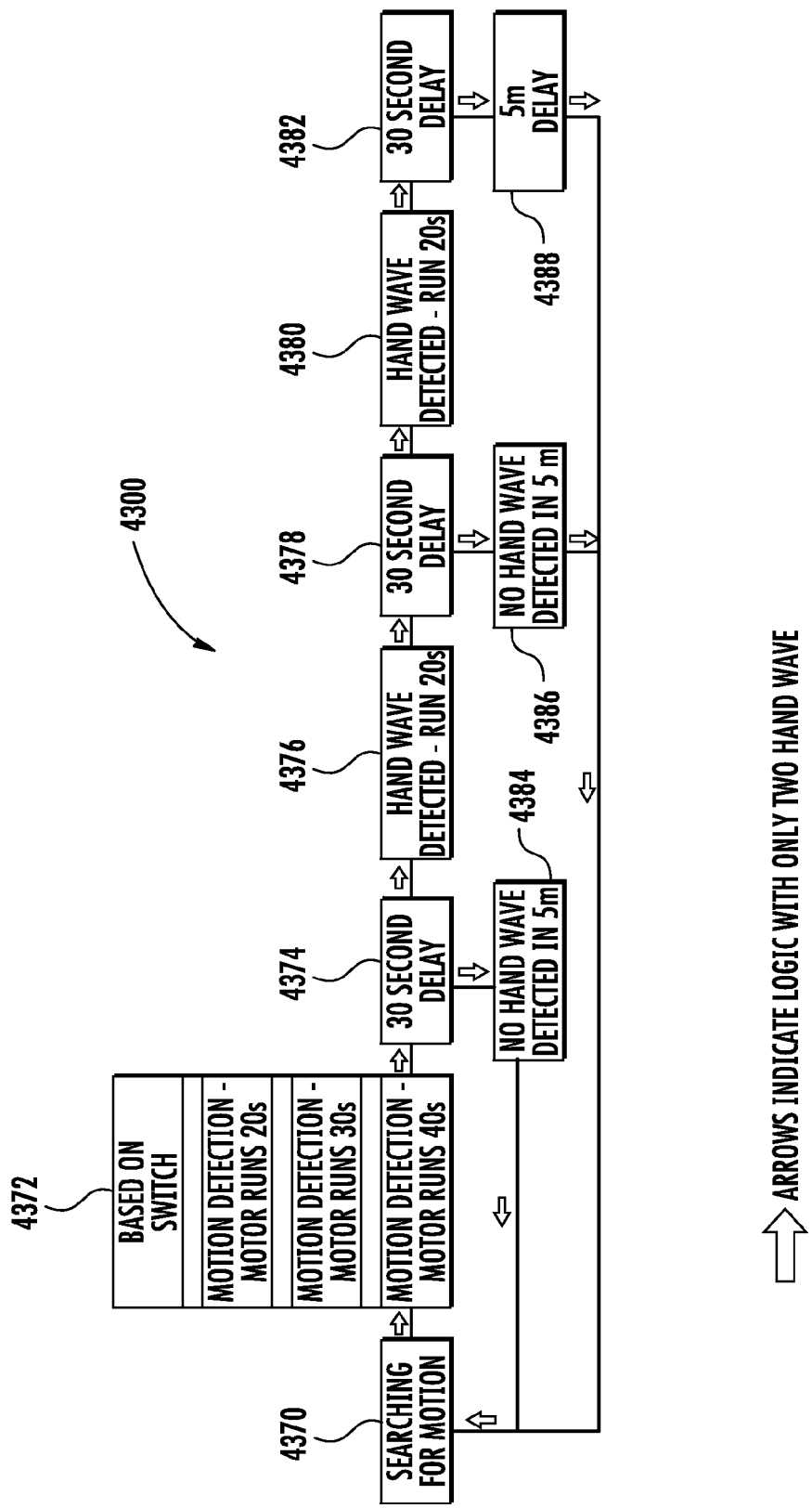
FIG. 43 is a flow diagram of a controller logic sequence for an air freshener dispenser having a user-request sensor and a motion sensor.

FIG. 43 illustrates a logic cycle flow diagram 4300 for an air freshener dispenser having a user-request and a motion sensor. Initially, the logic cycle 4300 includes the motion sensor searching for motion at step 4370. Upon the motion sensor sensing motion, the controller directs the motor to run the fan for either 20, 30, or 40 seconds, depending on the programmed logic for that particular dispenser, at step 4372. After the initial running of the fan, the controller then prevents the fan from running for 30 seconds at step 4374. After the 30 second delay, the controller will drive the fan for 20 seconds in response to receipt of a signal from the user-request (e.g., hand wave) sensor at steps 4376 and 4380. After running of the fan in response to a signal from the user-request sensor, the controller prevents the fan from running for 30 seconds at steps 4378 and 4382. After each running of the fan, if no signal from the user-request sensor is received within 5 minutes, as shown at steps 4384, 4386, and 4388, then the controller returns to the searching for motion step 4370, so as to thereafter direct running of the fan in response to a signal from the motion sensor and restart the logic sequence. Thus, the controller only runs the fan in response to a signal from the motion sensor at step 4372 and thereafter prevents running of the fan in response to a signal from the motion sensor for a period of at least 5 minutes.

Figure 44:
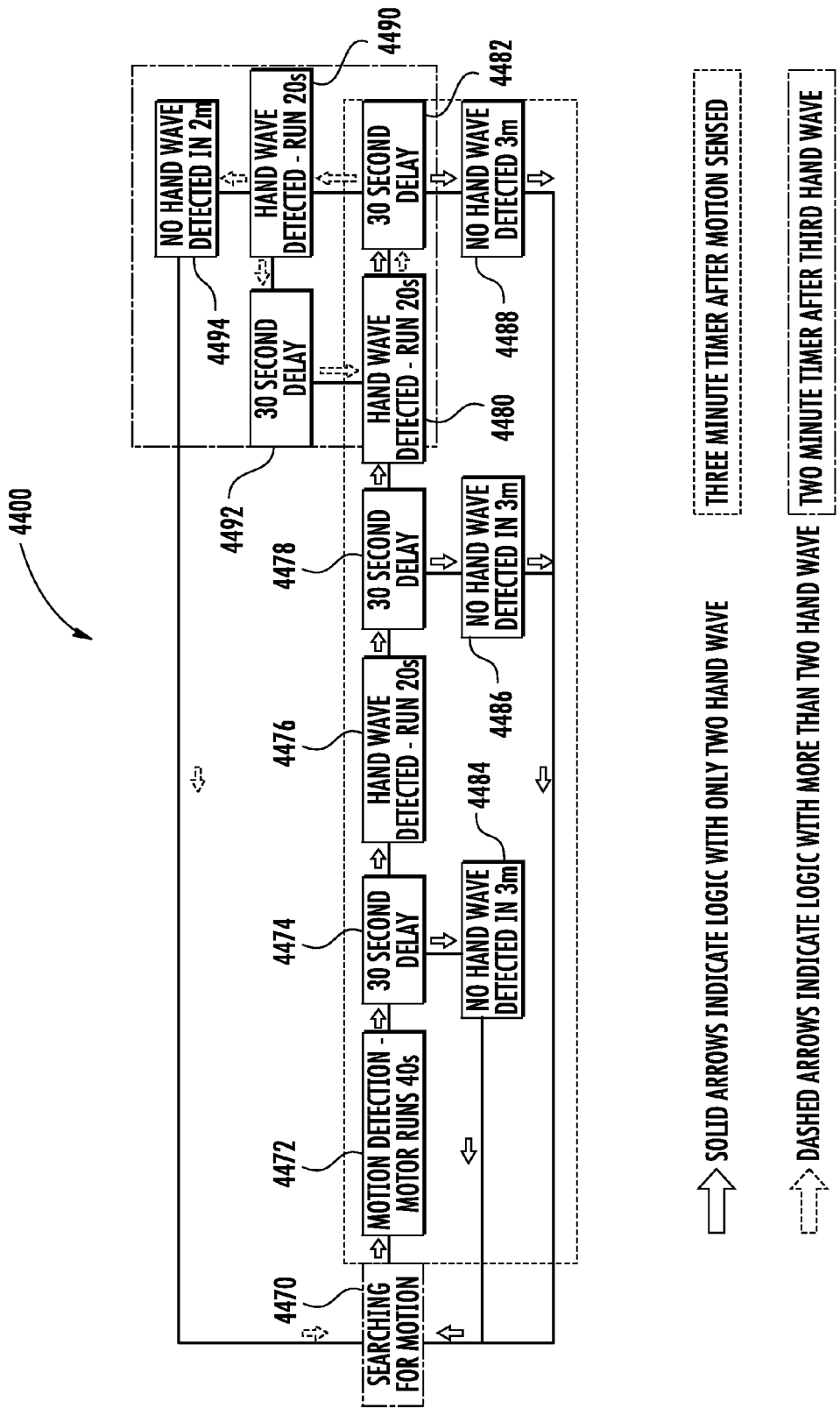
FIG. 44 is a flow diagram of a controller logic sequence for an air freshener dispenser having a user-request sensor and a motion sensor.

FIG. 44 illustrates a logic flow diagram 4400 for an air freshener dispenser having a user-request and a motion sensor. Initially, the logic cycle 4400 includes the motion sensor searching for motion at step 4470. Upon the motion sensor sensing motion, the controller directs the motor to run the fan for 40 seconds at step 4472. After the initial running of the fan, the controller then prevents the fan from running for 30 seconds at step 4474. After the 30 second delay, the controller will drive the fan for 20 seconds in response to receipt of a signal from the user-request (i.e., hand wave) sensor at steps 4476, 4480, and 4490. After running of the fan in response to a signal from the user-request sensor, the controller prevents the fan from running for 30 seconds at steps 4478, 4482, and 4492. After each running of the fan, if no signal from the user-request sensor is received within either 2 or 3 minutes, depending on the phase with the logic cycle, as shown at steps 4484, 4486, 4488, and 4494, the controller returns to the searching for motion step 4470, so as to thereafter direct running of the fan in response to a signal from the motion sensor and restart the logic cycle. Thus, the controller only runs the fan in response to a signal from the motion sensor at step 4472 and thereafter prevents running of the fan in response to a signal from the motion sensor for a period of at least 2 minutes after running of the fan.

Figure 45:
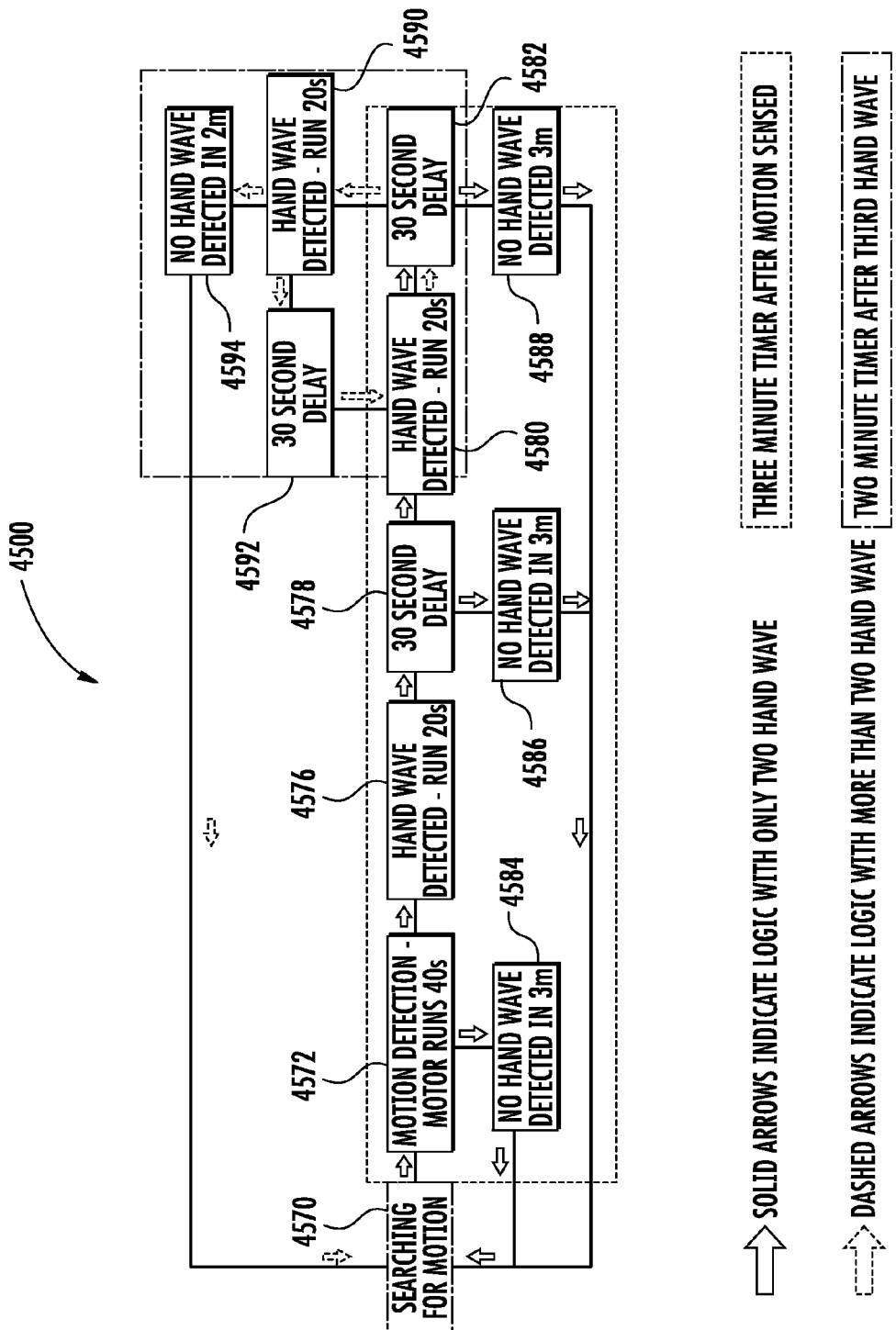
FIG. 45 is a flow diagram of a controller logic sequence for an air freshener dispenser having a user-request sensor and a motion sensor.

FIG. 45 illustrates a logic flow diagram 4500 for an air freshener dispenser having a user-request and a motion sensor. Initially, the logic cycle 4500 includes the motion sensor searching for motion at step 4570. Upon the motion sensor sensing motion, the controller directs the motor to run the fan for 40 seconds at step 4572. Immediately after driving the fan in response to detecting motion, the controller will drive the fan for 20 seconds in response to receipt of a signal from the user-request (i.e., hand wave) sensor at step 4576. After the initial running of the fan in response to a signal from the user-request sensor, the controller prevents the fan from running for 30 seconds at steps 4578, 4582, and 4592. After each running of the fan, if no signal from the user-request sensor is received within either 2 or 3 minutes, depending on the phase with the logic cycle, as shown at steps 4584, 4586, 4588, and 4594, the controller returns to the searching for motion step 4570, so as to thereafter direct running of the fan in response to a signal from the motion sensor and restart the logic cycle. Thus, the controller only runs the fan in response to a signal from the motion sensor at step 4572 and thereafter prevents running of the fan in response to a signal from the motion sensor for a period of at least 2 minutes after running of the fan.

Logic sequences used in the presently disclosed air freshener dispensers may be designed to conserve battery life and optimize product performance as well as to prevent excessive dispense of air freshener that may be unpleasant to users. Accordingly, in some embodiments, after the initial non-user-request based (i.e., second sensor based) activation of the fan, air freshener dispense can only be activated by a user request for a period of 2 to 6 minutes, depending on the dispenser.

In certain embodiments, the user-request sensor is configured to be triggered upon sensing one, two, three, or more waves of a user's hand. Thus, the logic sequence may be configured to initiate driving of the fan only in response to a certain number of hand waves by a user, depending on the position within the logic sequence. For example, as shown in FIG. 44, certain steps within the logic cycle 4400 require only two hand waves to be sensed (steps 4474 and 4480) to initiate driving the fan, while certain steps later in the sequence (steps 4490 and 4480, after delay 4492) require at least three hand waves to be sensed to initiate driving the fan.

In certain embodiments, the controller is configured to continuously drive the fan at a certain rate to release a relatively low air freshener from the dispenser continuously, and to drive the fan at a higher rate in response to receipt of a signal from the at least one sensor, to provide a burst of air freshener.

Figure 7:
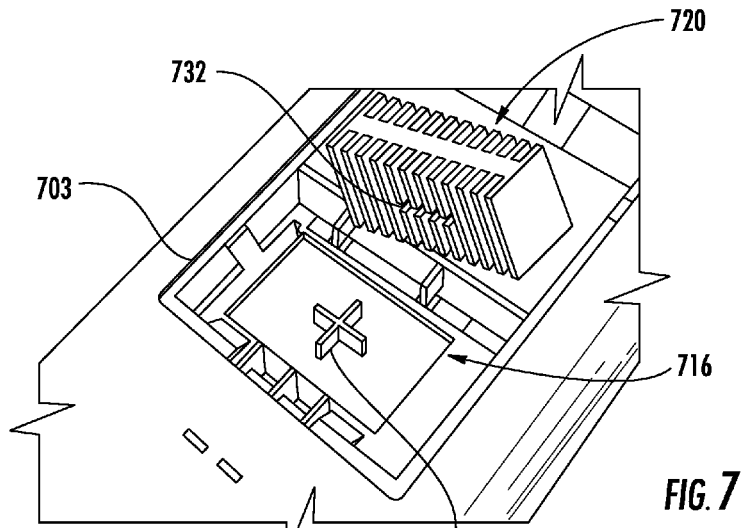
FIG. 7 is a perspective view of a cavity of an air freshener dispenser and a corresponding air freshener cartridge.

In certain embodiments, as shown in FIG. 7, the housing 703 of the air freshener dispenser includes at least one projection 730 within the cavity 716 that is configured for mating engagement with a recess 732 of the cartridge 720. The one or more projections advantageously may assist in aligning the cartridge within cavity and housing to encourage proper airflow through and around the cartridge, to provide ease of access to and/or removal of the cartridge by maintenance personnel, to ensure that the cartridges are used with the appropriate dispenser (i.e., to prevent the use of cartridges designed for use with other dispensers), and to mitigate or prevent the use of unauthorized cartridge refills with the dispenser.

Figure 8A:
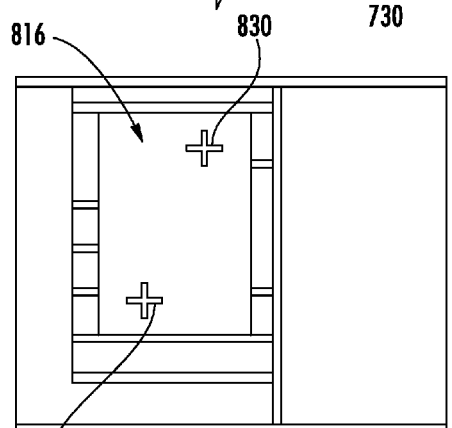
FIG. 8A is a top view of a cavity of an air freshener dispenser.
Figure 8B:
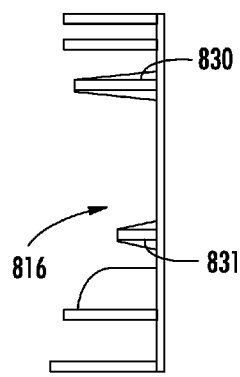
FIG. 8B is a side view of the cavity of FIG. 8A.
Figure 9:
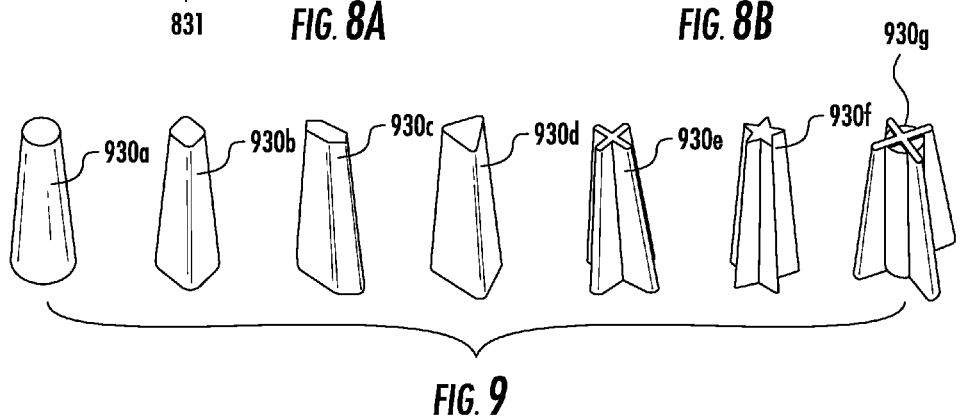
FIG. 9 is a perspective view of various cavity projection geometries.

A variety of suitable projection geometries and configurations may be used. For example, the projection may include one or more ribs or posts located within the cavity. For example, FIG. 7 illustrates a cavity having a cross-shaped projection 730 centrally located within the cavity 716 and a cartridge 720 having a corresponding cross-shaped recess 732. For example, FIGS. 8A and 8B illustrate a cavity 816 having two tapered cross-shaped posts 830, 831 of different heights located near opposite corners of the cavity 816. For example, having posts of different heights may enable easier removal of the cartridge, as explained further with reference to FIGS. 28A and B. Various projection geometries 930a, 930b, 930c, 930d, 930e, 930f, 930g are shown at FIG. 9. As shown at FIG. 9, the projections may be tapered. In other embodiments, the projections have a consistent cross-section over their length. In some embodiments, the projection may have a circular, oval, elliptical, triangular, cross-shaped, star-shaped, or more complex shaped cross section.

Figure 10:
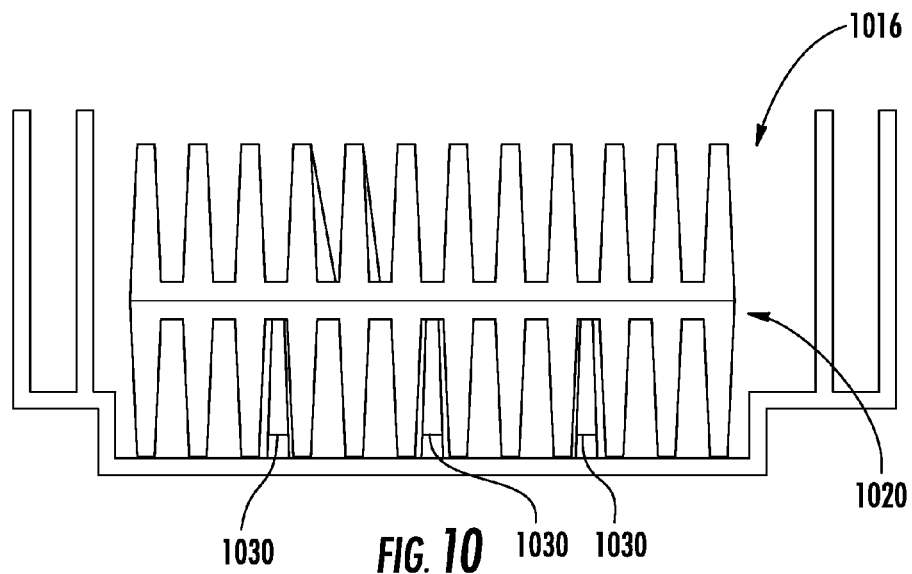
FIG. 10 is a cross-sectional view of a cavity of an air freshener dispenser containing a cartridge with bottom locating features.
Figure 11:
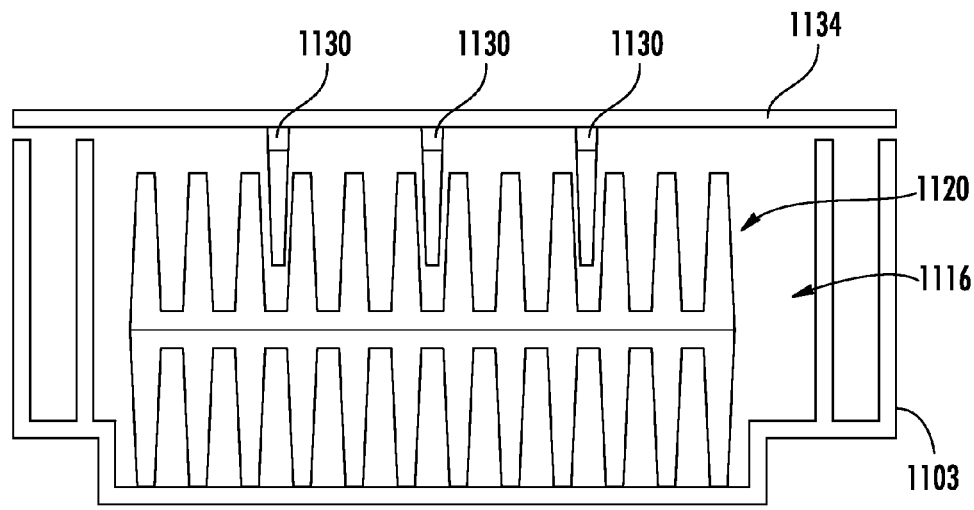
FIG. 11 is a cross-sectional view of a cavity of an air freshener dispenser containing a cartridge.
Figure 12:
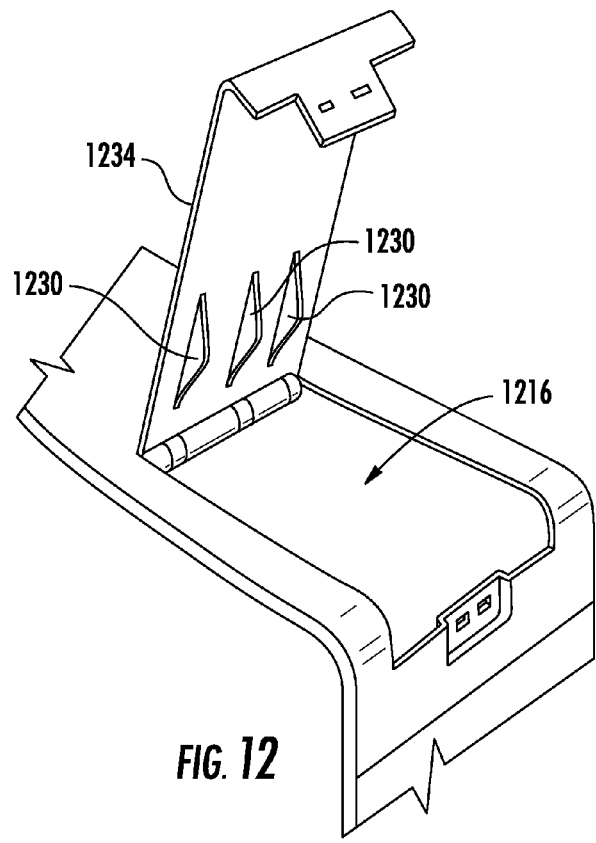
FIG. 12 is a perspective view of a cavity access door in a housing of an air freshener dispenser with top locating features.

As shown in FIG. 10, the cavity 1016 may contain three rib-like projections 1030 that are configured to mate with airflow channels of the cartridge 1020. In certain embodiments, as shown in FIG. 11, the housing 1103 includes a door 1134 that provides access to the cavity 1116 and the projection(s) 1130 is located on the door 1134. For example, the door may be a hinged or slidable design and may provide access within the housing to the battery compartment and/or other components, as well as to the cavity. As shown in FIG. 12, the door 1234 provides access to the cavity 1216 and includes three rib-like projections 1230 for mating with corresponding recesses of a cartridge loaded into the cavity 1216. As shown in FIG. 12, the rib-like projections 1230 of the cavity door or base may have a curvilinear profile to minimize the contact between the cartridge surfaces and the projections such that airflow through the airflow channels of the cartridge that receive the projections is minimally restricted. In some embodiments, projections are provided on both the base and door of the cavity.

In certain embodiments, as shown in FIGS. 15 and 17, the cavity 1516 has one or more recesses 1544 that are configured for mating engagement with one or more projections 1545 of the cartridge 1520. For example, the projections 1545 of the cartridge 1520 may be configured for a snap-fit engagement with the cavity recesses 1544.

In an alternative embodiment, the positions of the one or more projections and the mating recesses are reversed. That is, the cartridge may include one or more projections, and at least one wall structure defining the cavity includes the associated one or more recesses for mating engagement with the one more projections.

As shown in FIG. 16, a sensor or switch 1546 may be associated with the cavity 1516 and configured to detect the presence of a cartridge in the cavity 1516. In some embodiments, the sensor/switch 1546 is configured send a signal to the controller when a cartridge 1520 is introduced to the cavity 1516 and/or to send a signal to the controller when the cartridge 1520 is removed from the cavity 1516 or depletes to a certain extent. For example, as air freshening substance is released from the cartridge, the cartridge may shrink, such that a switch or other sensor can determine the depletion status of the cartridge.

Air Freshener Cartridges

Air freshener cartridges are also provided herein. As discussed above, an air freshener cartridge may be any suitable self-supporting solid substance containing an air freshening substance, or a semi-solid substance containing an air freshening substance and that is supported by a container, and assemblies containing such substances, that are configured to release the air freshening substance by volatilization and diffusion-based release thereof. For example, cartridges may have any suitable composition, size, and shape to fit within the dispenser such that the desired rate and intensity of release of the air freshening substance is achieved. In some embodiments, cartridges for use with the presently described air freshener dispensers may include gel-based, wax-based, ceramic-based, or polymer-based substances containing or impregnated with an air freshening substance. In some embodiments, the cartridges are monolithic structures, such as blocks or other designs having airflow channels. In some embodiments, the cartridges have a container, such as a cup, containing a gel-based air freshening substance. In some embodiments, the cartridge includes a plurality of air freshening beads, such as loose or sintered beads. For example, a cartridge may include a plurality of loose beads contained within a mesh bag. Cartridges described herein may be manufactured by any suitable means, such as by injection-molding or extrusion.

In certain embodiments, as shown in FIGS. 18A-18E, an air freshener cartridge 1820 includes a body 1848 containing a matrix material impregnated with an air freshening substance selected from an odor-combatting composition, a fragrance, and a combination thereof. Thus, the air freshening substance may have a scent or be unscented.

In certain embodiments, the body of the cartridge contains the air freshening substance in an amount of from about 1 percent by weight to about 75 percent by weight. In some embodiments, the body contains the air freshening substance in an amount of from about 10 percent by weight to about 50 percent by weight. In some embodiments, the body contains the air freshening substance in an amount of from about 15 percent by weight to about 45 percent by weight. In some embodiments, the body contains the air freshening substance in an amount of from about 20 percent by weight to about 30 percent by weight. In one embodiment, the body contains the air freshening substance in an amount of about 25 percent by weight. In one embodiment, the body contains the air freshening substance in an amount of about 35 percent by weight. The ratio of air freshening substance to matrix material in the cartridge body may be selected to provide the desired release of the air freshener substance.

The matrix material and air freshening substance may be selected from various suitable materials known in the art. For example, the matrix material may be a polymer, such as ethylene-vinyl acetate (EVA). Suitably, EVA has no odor but can be impregnated with a fragrance or odor-combatting composition. Additionally, EVA approaches elastomeric materials in softness and flexibility, yet can be processed like a thermoplastic. In certain embodiments, the EVA polymer of the cartridge body has a number average molecular weight in the range of about 10,000 Daltons to about 100,000 Daltons, or from about 22,000 to about 87,000 Daltons. Other elastomeric or thermoplastic polymers known in the art may also be used in the cartridge body. For example, the polymer of the cartridge body may include ethyl vinyl alcohol, high density polyethylene, low density polyethylene, polystyrene, acrylic polymers, polycarbonates, polyurethanes, nylons, and mixtures and copolymers thereof.

The matrix material may be impregnated with one or more suitable air freshening substances known in the art. For example, suitable air freshening substances may be selected from those compiled by the U.S. Food and Drug Administration in Title 21 of the Code of Federal Regulations, Sections 172.5 10 and 172.5 15. In certain embodiments, the air freshening substance is selected from the group consisting of benzaldehydes, phenols, cinnamic aldehydes and esters, octadienes, dienes, cyclohexadienes, terpenes, and combinations thereof. In some embodiments, the air freshening substance includes triethylene glycol, a bleach, or hydrogen peroxide. Fragrance oils are also suitable for use alone or in combination with other fragrance chemicals. Suitable fragrance oils include, for examples spice oil, flower oil, and fruit oil. Other suitable fragrances include, but are not limited to, benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol. In certain embodiments, the air freshening substance may include one or more additives, such as hindered amines or antioxidants.

The air freshener cartridge body may be sized and shaped to provide the desired passive and fan-induced release of the air freshener substance. For example, the cartridge body may have a particular volume and surface area to provide a desired release profile. The cartridge body may also be sized and shaped to have one or more recesses for mating engagement with projection(s) of the cavity of a dispenser. Various cartridge body designs are illustrated at FIGS. 15-33.

In certain embodiments, the cartridge body has a volume of from about 0.1 in$^3$ (1,600 mm$^3$) to about 2.5 in$^3$ (41,000 mm$^3$). In certain embodiments, the cartridge body has a volume of from about 0.4 in$^3$ (7,000 mm$^3$) to about 1.4 in$^3$ (23,000 mm$^3$). For example, the cartridge body may have a volume of from about 0.75 in$^3$ (12,000 mm$^3$) to about 1 in$^3$ (20,000 mm$^3$), from about 0.85 in$^3$ (14,000 mm$^3$) to about 1 in$^3$ (20,000 mm$^3$), or of about 0.9 in$^3$ (15,000 mm$^3$). In certain embodiments, the cartridge body has a surface area of from about 2.0 in$^2$ (1,300 mm$^2$) to about 40 in$^2$ (26,000 mm$^2$). In certain embodiments, the cartridge body has a surface area of from about 9 in$^2$ (6,000 mm$^2$) to about 28 in$^2$ (18,000 mm$^2$). For example, the cartridge body may have a surface area of from about 14 in$^2$ (9,000 mm$^2$) to about 21 in$^2$ (14,000 mm$^2$), from about 17 in$^2$ (11,000 mm$^2$) to about 21 in$^2$ (14,000 mm$^2$), or of about 20 in$^2$ (13,000 mm$^2$). In some embodiments, the cartridge body has a weight of up to about 20 g, such as up to about 15 g. In certain embodiments, the cartridge body has a weight of from about 6 g to about 20 g. For example, the cartridge may have a weight of from about 11 g to about 15 g, from about 11.5 g to about 13 g, or from about 14 g to about 15 g.

The cartridge body may have any desired shape and geometry selected to provide to the desired release profile of the air freshening substance impregnated in the matrix material. In certain embodiments, as shown in FIG. 18A, the body 1848 of the cartridge 1820 includes a plurality of ribs 1850 extending from a substrate 1854 and forming airflow channels 1852 therebetween. In certain embodiments, from about 3 to about 30 ribs extend from each surface of a substrate (i.e., ribs extend from both the top surface and the opposed bottom surface of the substrate). In other embodiments, from about 3 to about 30 ribs extend from one surface of a substrate. For example, the airflow channels may extend from one edge of the body to another opposed edge of the body, such that the channels may be aligned with the airflow path within the housing when the cartridge is loaded into a cavity of a dispenser.

Various cartridge body, rib, and substrate designs may be used, depending on the particular cavity design and desired release characteristics. Three rib and substrate designs are shown in FIGS. 18-20.

In one embodiment, as shown in FIG. 18, the 16 ribs 1850 extending from the top and bottom surfaces of the substrate (8 rib pairs) each have a substantially rectangular surface and are tapered from a wider rib base at the substrate 1854 to a thinner rib face. As illustrated in FIGS. 18B, 18C, and 18D, the body 1848 of the cartridge 1820 may have a height (h) of about 18 mm, a length (l) of about 44 mm, a width (w) of about 26 mm, a rib face thickness ($t_i$) of about 3 mm, a rib base thickness ($t_{ii}$) of about 5 mm, a base air channel gap ($d_i$) of about 0.9 mm, a face air channel gap ($d_{ii}$) of about 2 mm, a volume of about 15,500 mm$^3$, and a surface area of about 9,570 mm$^2$.

In another embodiment, as shown in FIG. 19, the 24 ribs 1950 extending from the top and bottom surfaces of the substrate (12 rib pairs) each have a substantially rectangular surface and are tapered from a wider rib base at the substrate 1954 to a thinner rib face. As illustrated in FIGS. 19B, 19C, and 19D, the body 1948 of the cartridge 1920 may have a height (h) of about 18 mm, a length (l) of about 44 mm, a width (w) of about 26 mm, a rib face thickness ($t_i$) of about 2.6 mm, a rib base thickness ($t_{ii}$) of about 2.9 mm, a base air channel gap ($d_i$) of about 0.8 mm, a face air channel gap ($d_{ii}$) of about 1.4 mm, a volume of about 15,400 mm$^3$, and a surface area of about 13,100 mm$^2$. Thus, by increasing the number of ribs provided in a cartridge having a constant overall height, length, and width, the surface area and volume of the body may be increased.

Figures 20A, 20B, 20C, 20D:
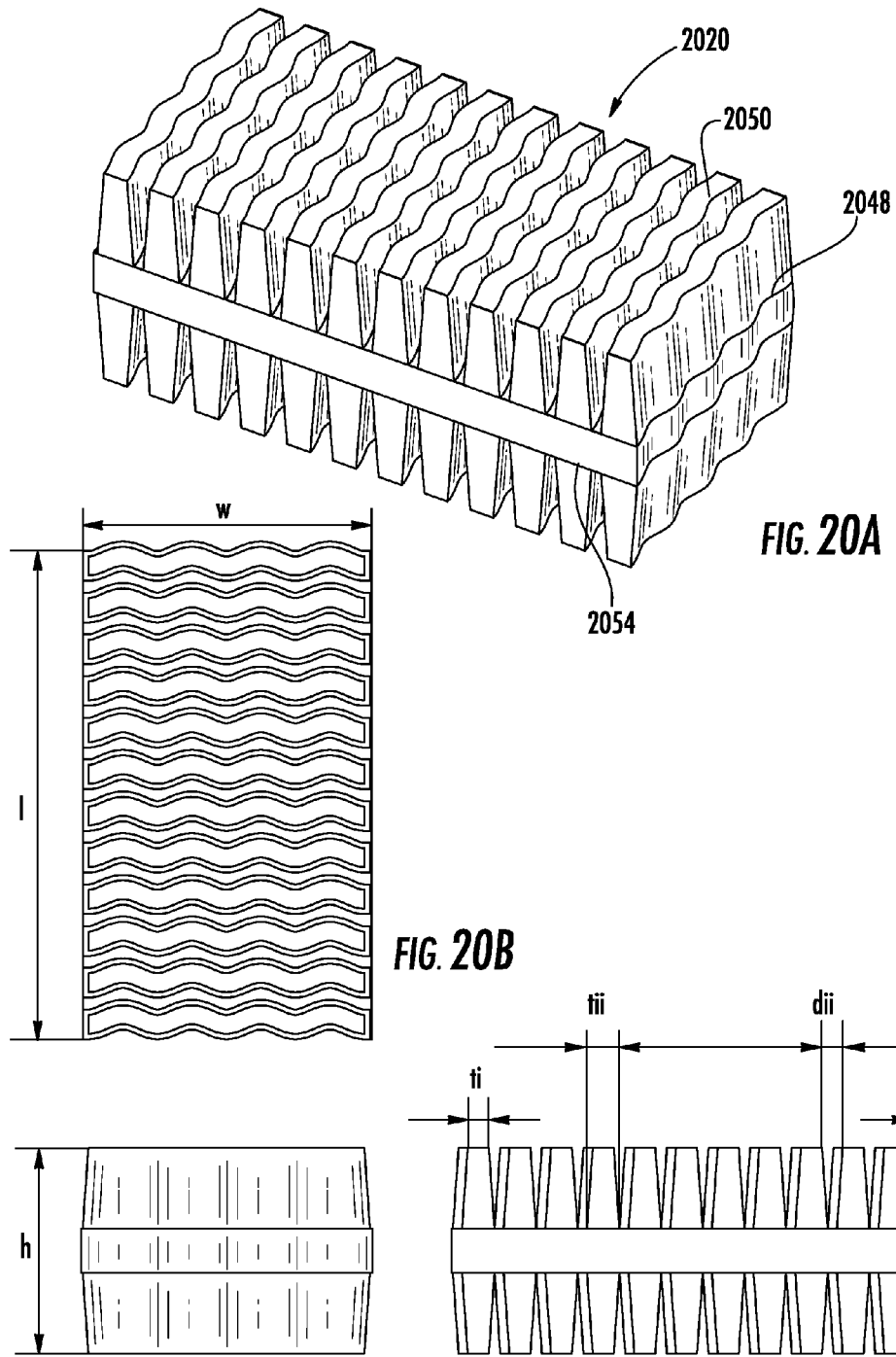
FIG. 20A is a perspective view of an air freshener cartridge.
FIG. 20B is a top view of the cartridge of FIG. 20A.
FIG. 20C is a side view of the cartridge of FIG. 20A.
FIG. 20D is another side view of the cartridge of FIG. 20A.
Figure 20E:
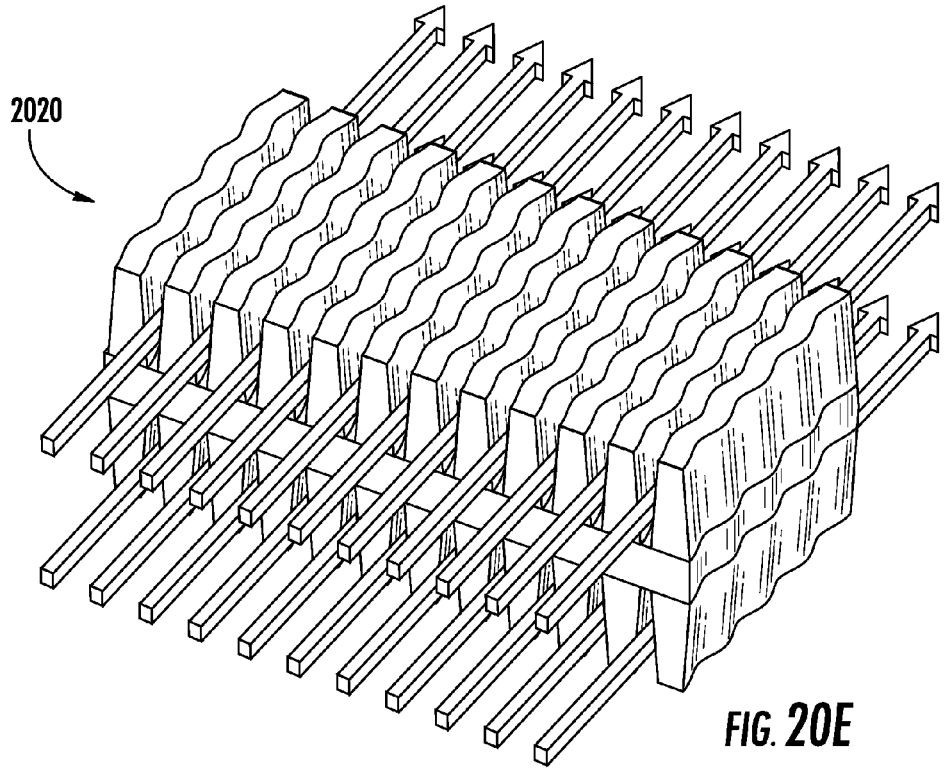
FIG. 20E a perspective view showing airflow through the cartridge of FIG. 20A.
Figure 20F:
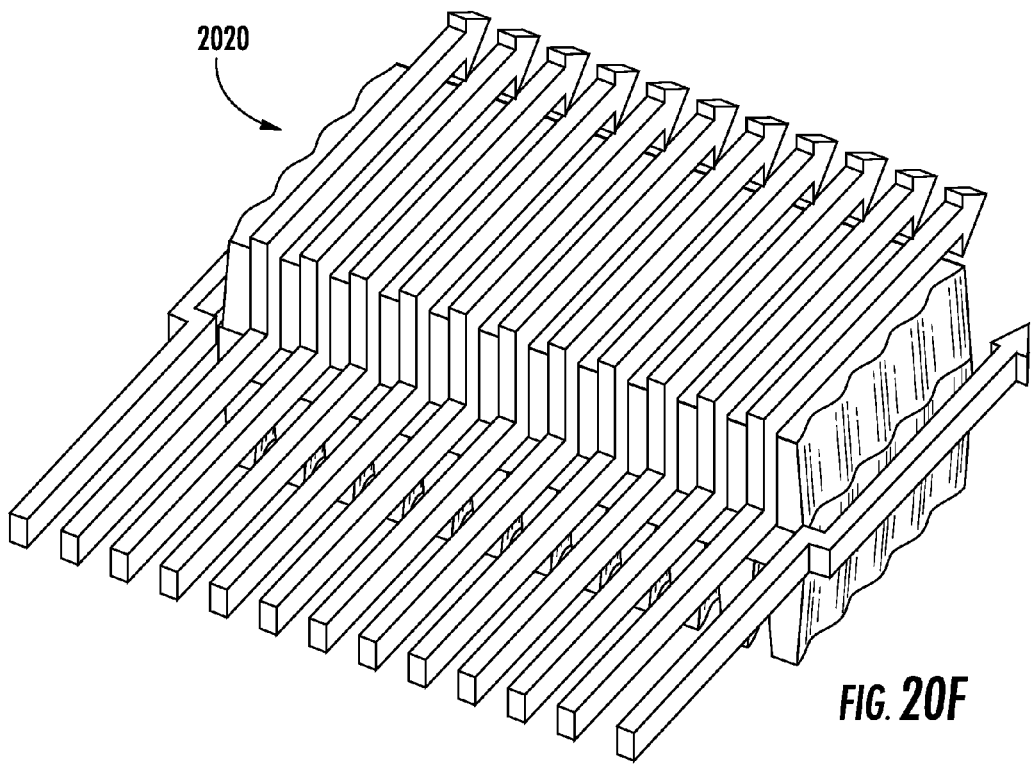
FIG. 20F is a perspective view showing airflow around the cartridge of FIG. 20A.

In another embodiment, as shown in FIG. 20, the ribs 2050 each have a serpentine shaped surface and are tapered from a wider rib base at the substrate 2054 to a thinner rib face. As illustrated in FIGS. 20B, 20C, and 20D, the body 2048 of the cartridge 2020 may have a height (h) of about 18 mm, a length (l) of about 44 mm, a width (w) of about 26 mm, a rib face thickness ($t_i$) of about 1.8 mm, a rib base thickness ($t_{ii}$) of about 2.2 mm, a base air channel gap ($d_i$) of about 1.6 mm, a face air channel gap ($d_{ii}$) of about 2.0 mm, a volume of about 12,500 mm$^3$, and a surface area of about 12,600 mm$^2$.

Increased air freshening substance may be released from a cartridge having increased surface area because the air freshening substance may be volatized at a higher rate. However, a cartridge having increased surface area may deplete more quickly than a cartridge of the same composition with lower surface area.

In certain embodiments, the cartridge body has a height of from about 2.5 mm to about 25.5 mm. In certain embodiments, the cartridge body has a length of from about 2.5 mm to about 76.5 mm. In certain embodiments, the cartridge body has a width of from about 2.5 mm to about 76.5 mm.

In some embodiments, the substrate of a cartridge body has a thickness of about 0.01 inch (0.25 mm) to about 0.5 inch (13 mm). In certain embodiments, the substrate of a cartridge body has a thickness of about 1/16 inch (1.6 mm) to about 1/4 inch (6.4 mm). In some embodiments, the ribs extending from the substrate have an average thickness of about 0.01 inch (0.25 mm) to about 0.5 inch (13 mm). In some embodiments, the ribs extending from the substrate have an average thickness of about 1/8 inch (3.2 mm) to about 1/32 inch (0.8 mm). In certain embodiments, the thickness of the ribs decreases from a greatest thickness at the substrate to a smallest thickness at the face of the cartridge. For example, the ribs may have a thickness at the substrate of from about 0.76 mm to about 7.62 mm and a thickness at the face of the cartridge of from about 1.02 mm to about 6.35 mm.

In certain embodiments, the cartridge body and ribs are designed to provide an average air channel gap thickness between adjacent ribs of from about 0.76 mm to about 12.7 mm. For example, the air gap may be tapered such that the thickness of the air channel gap is greatest at the face of the cartridge and smallest at the substrate. For example, the air channel gap may have a thickness at the substrate of from about 0.76 mm to about 12.7 mm and a thickness at the face of the cartridge of from about 1.12 mm to about 11.43 mm.

In some embodiments, as shown in FIGS. 15 and 17 the cartridge 1520 has flexible features 1542 configured to interact with a sensor 1546 in the cavity 1516.

Figure 21:
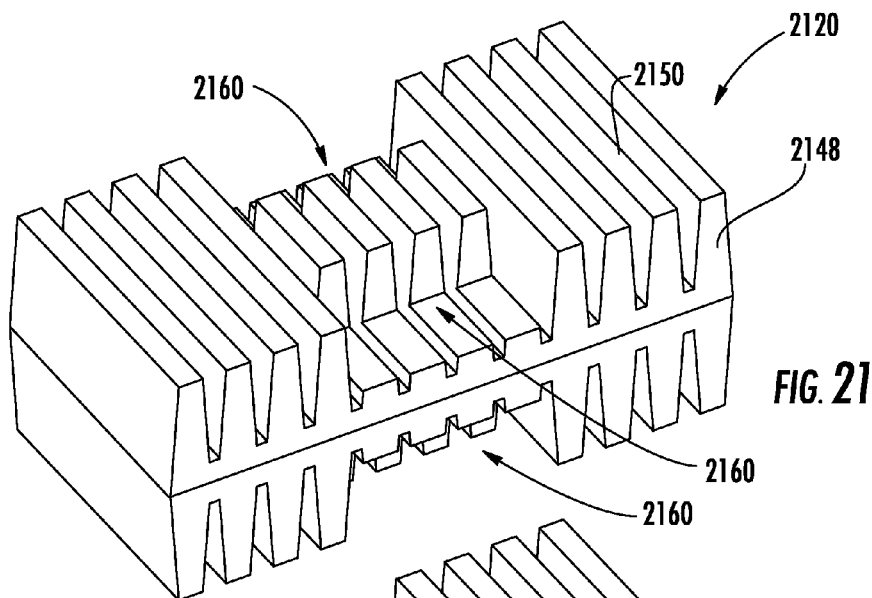
FIG. 21 is a perspective view of an air freshener cartridge.
Figure 22:
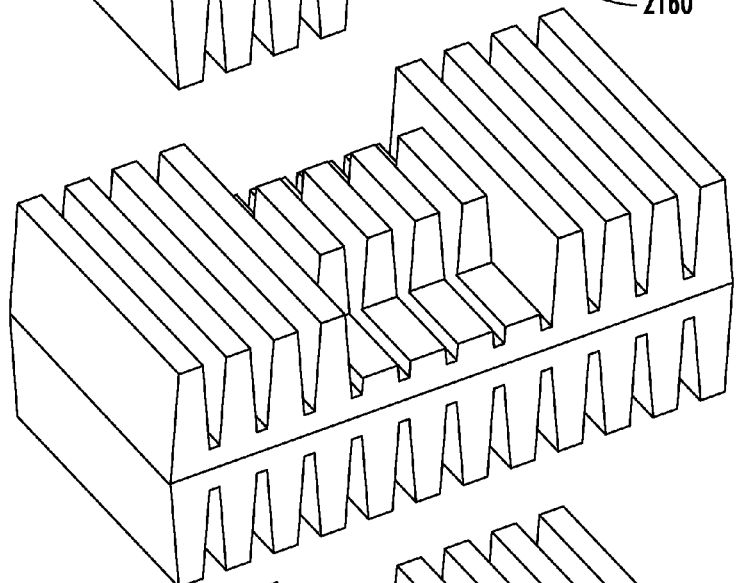
FIG. 22 is a perspective view of an air freshener cartridge.
Figure 23:
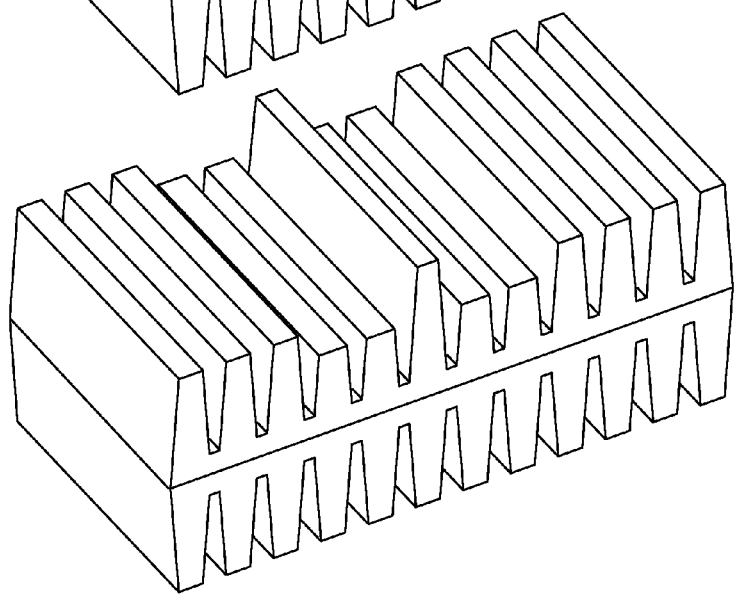
FIG. 23 is a perspective view of an air freshener cartridge.
Figure 24:
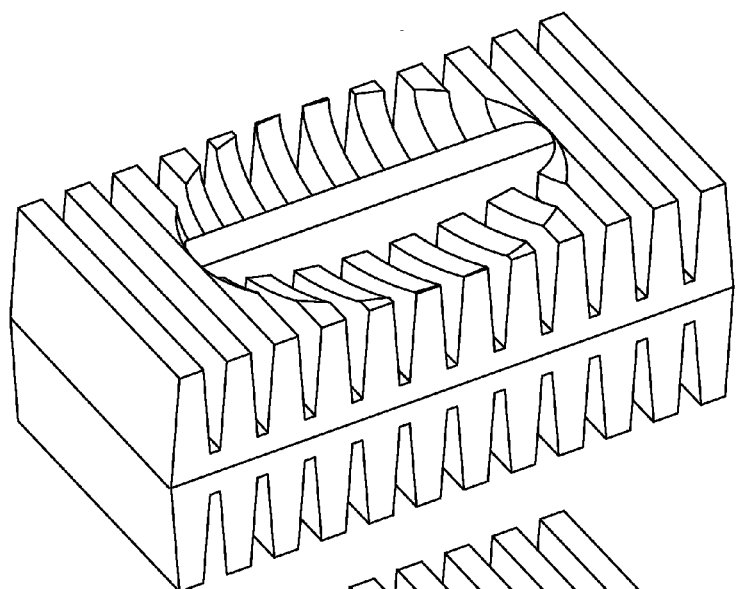
FIG. 24 is a perspective view of an air freshener cartridge.
Figure 25:
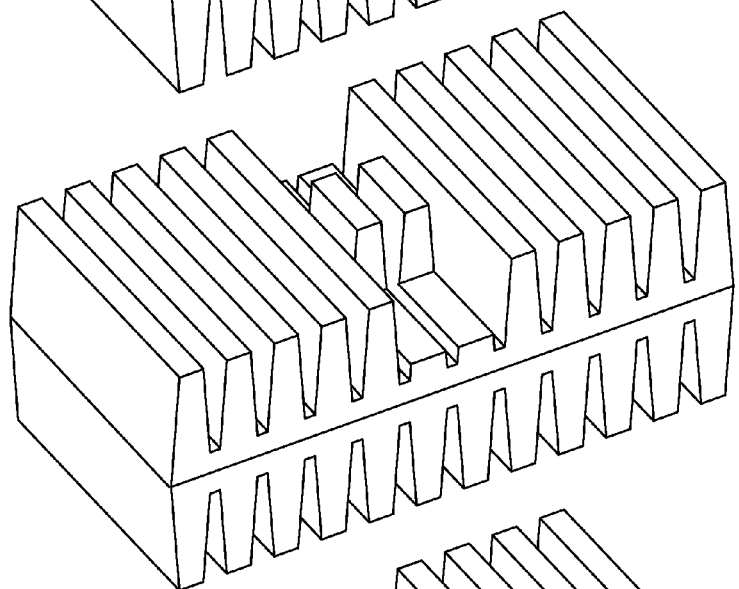
FIG. 25 is a perspective view of an air freshener cartridge.
Figure 26:
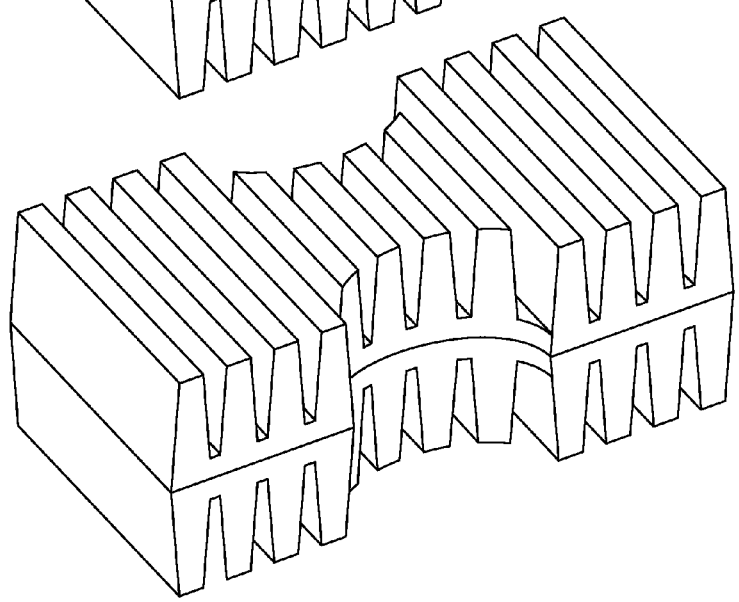
FIG. 26 is a perspective view of an air freshener cartridge.
Figure 27:
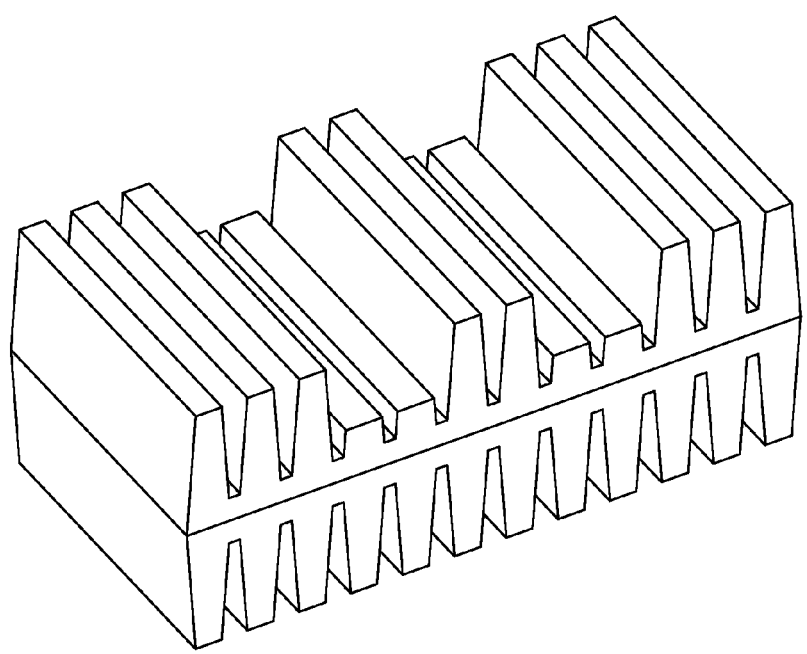
FIG. 27 is a perspective view of an air freshener cartridge.

In certain embodiments, the cartridge further includes a handling feature to assist in installation and removal of the cartridge in/from a cavity and/or to allow a handler to avoid touching the body portion of the cartridge. In certain embodiments, as shown in FIGS. 21-27, the handling feature may be integrated into the cartridge body. For example, the handling feature may be molded into any of the cartridge body designs described herein. In certain embodiments, the handling feature may include one or more indentations or extended tabs that allow for gripping the cartridge body. As shown in FIG. 21, the cartridge 2120 is similar to the cartridge design of FIG. 19, but includes four indentations 2160, wherein the central 4 ribs of the cartridge body 2148 have a length of about one-third the length of the other ribs 2150, thereby providing a gripping feature for a user. Other embodiments of gripping features that are formed by the cartridge body are illustrated in FIGS. 22-27.

In other embodiments, a handling feature may be formed by a structure that is distinct from the cartridge body, such as a pull tab or other feature. Such handling features may formed of a similar material to the cartridge body or a different material, such as silicone or another material, so that the user can avoid touching the cartridge body.

Figure 28A:
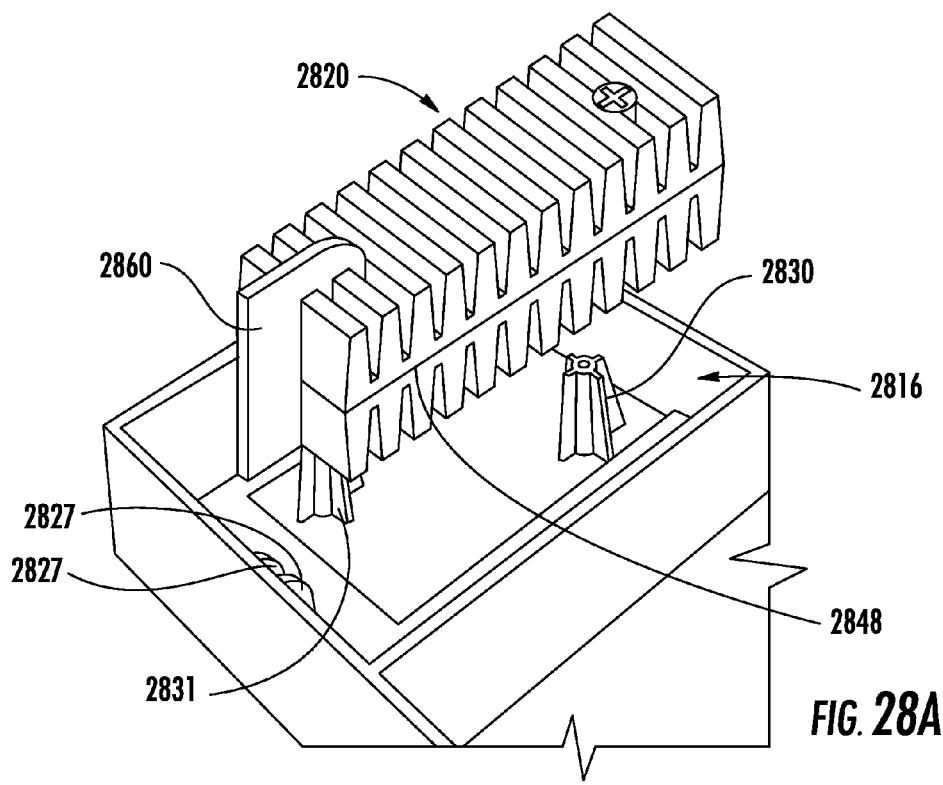
FIG. 28A is an exploded perspective view of an air freshener cartridge and cavity of a dispenser.
Figure 28B:
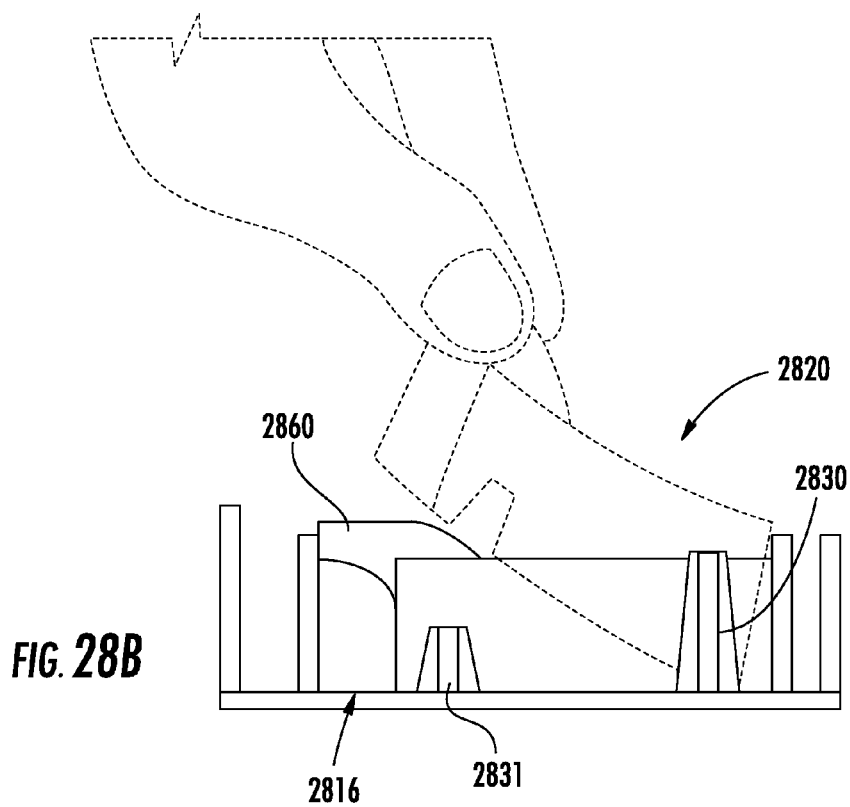
FIG. 28B is a perspective view of a user removing the air freshener cartridge of FIG. 28A from the cavity of the dispenser.

In certain embodiments, as shown in FIGS. 28A and 28B, the cartridge 2820 includes a fin 2860 extending from one end of the cartridge 2820 to provide both a gripping feature for removal (i.e., portion extending above the top surface of the cartridge 2820 when the cartridge 2820 is loaded in the cavity 2816) and to orient the cartridge 2820 within the cavity 2816 (i.e., portion extending past the length of the cartridge body 2848 is configured to fit between projections 2827 within the cavity 2816. Thus, as shown in FIG. 28B, the gripping feature 2860 may be gripped by a user for cartridge removal. Additionally, as also discussed with reference to FIGS. 8A and 8B, in FIGS. 28A and 28B, the cavity includes two tapered cross-shaped posts 2830, 2831 of different heights (one of approximately the height of the cartridge, and one approximately half that height) located near opposite corners of the cavity 2816. As shown in FIG. 28B, the difference in heights of the posts 2830, 2831 enables easier removal of the cartridge 2820 from the cavity 2816.

Figures 29A, 29B:
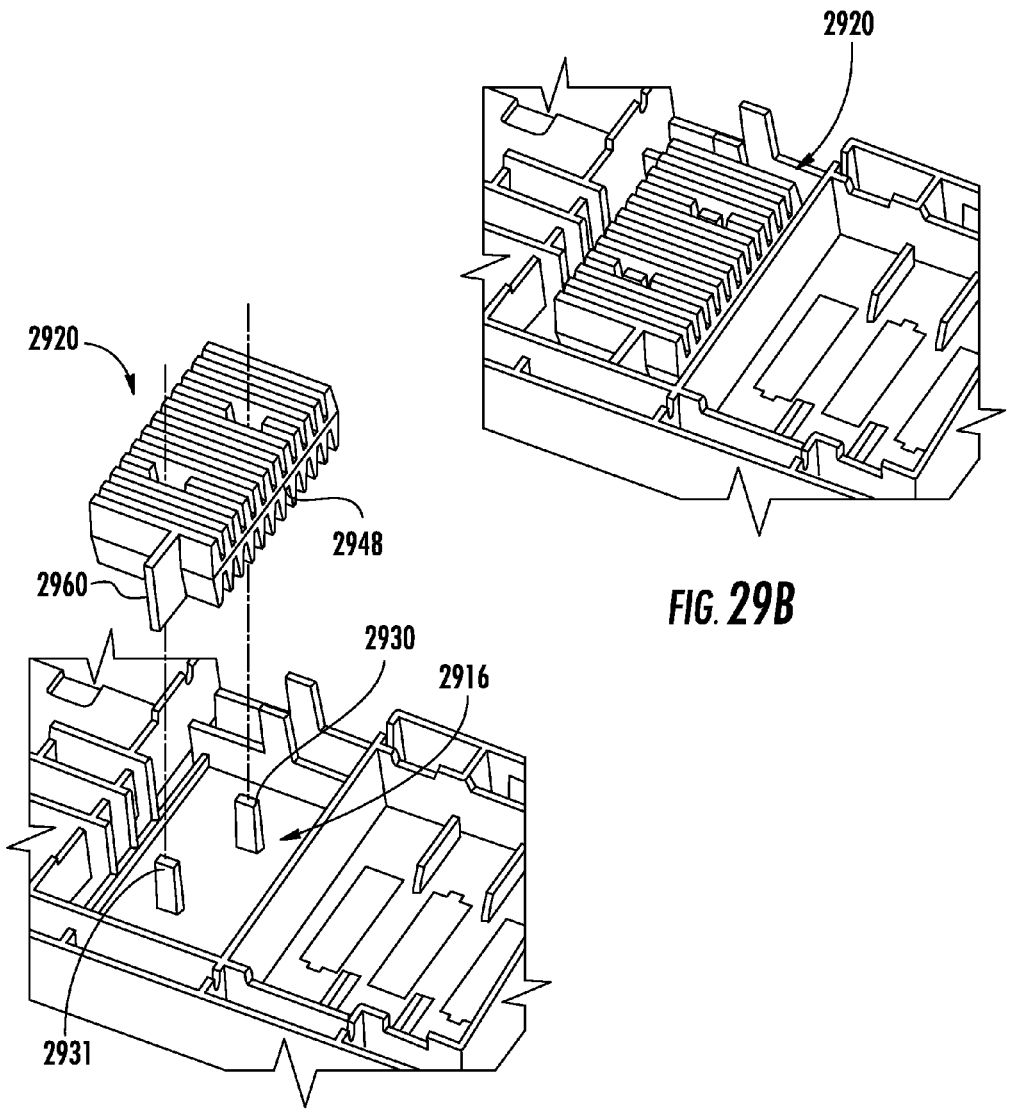
FIG. 29A is an exploded perspective view of an air freshener cartridge and cavity of a dispenser.
FIG. 29B is a perspective view of the air freshener cartridge loaded in the cavity of FIG. 29A.

Another embodiment of a gripping feature is shown in FIGS. 29A and 29B, which illustrate a cartridge 2920 that is similar to the cartridge of FIG. 19, having two recesses therethrough for mating engagement with the projections 2930, 2931 of dispenser cavity 2916. The cartridge 2920 includes a gripping feature 2960 extending from one end of the cartridge 2920, past the length of the cartridge body 2948. In the embodiment of the cavity 2920 shown, the gripping feature 2960 is accessible by a user to facilitate removal of the cartridge 2920 from the cavity 2916.

Another embodiment of a gripping feature is shown in FIGS. 30A, 30B, 30C and 30D, which illustrate a cartridge 3020 having a fin 3060 extending from one of the ribs 3050 of the cartridge body 3048, past the height of the cartridge body 3048. For example, the fin 3060 may include a living hinge, i.e., an integral hinge. The cartridge 3020 may be loaded into a cavity 3016, such that upon closing of the cavity door 3034, the fin 3060 is bent at the living hinge to accommodate the cavity door 3034. When the cavity door 3034 is opened, the fin 3060 may be gripped by a user to remove the cartridge 3020 from the cavity 3016.

Figure 31:
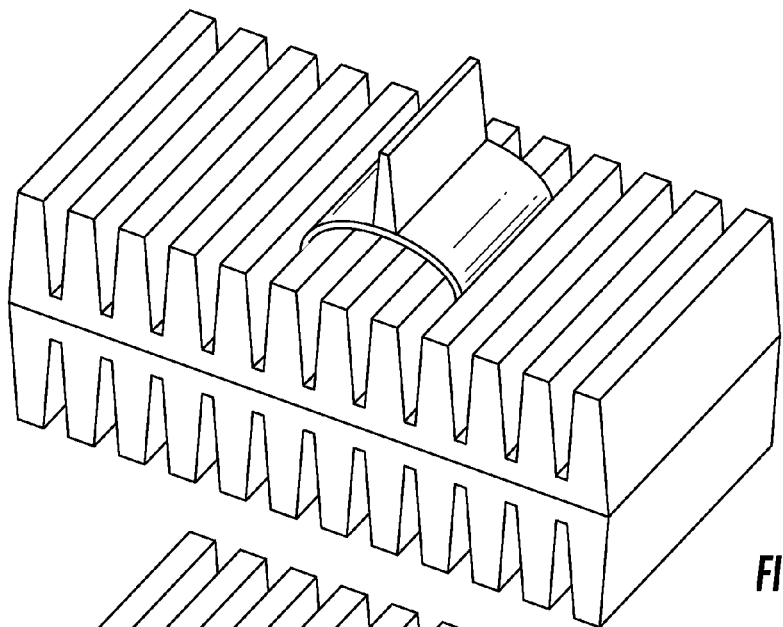
FIG. 31 is a perspective view of an air freshener cartridge having a handling feature.
Figure 32:
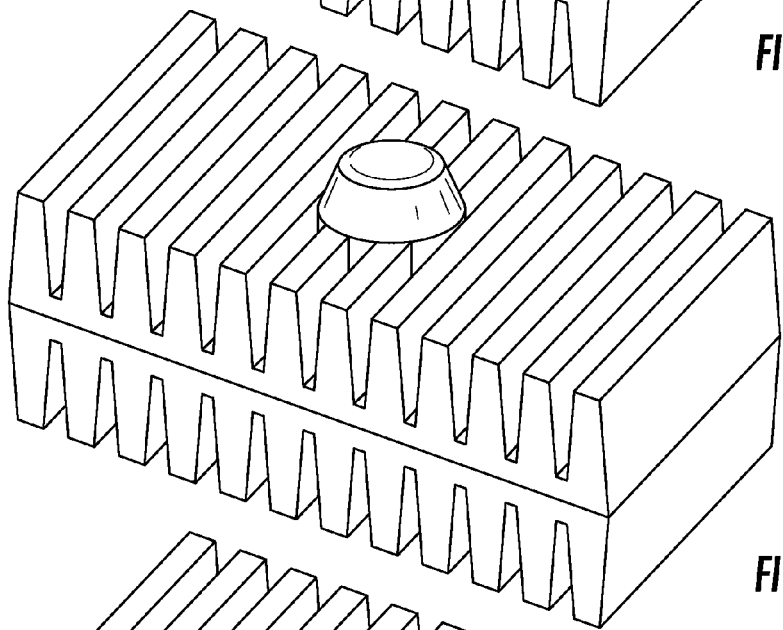
FIG. 32 is a perspective view of an air freshener cartridge having a handling feature.
Figure 33:
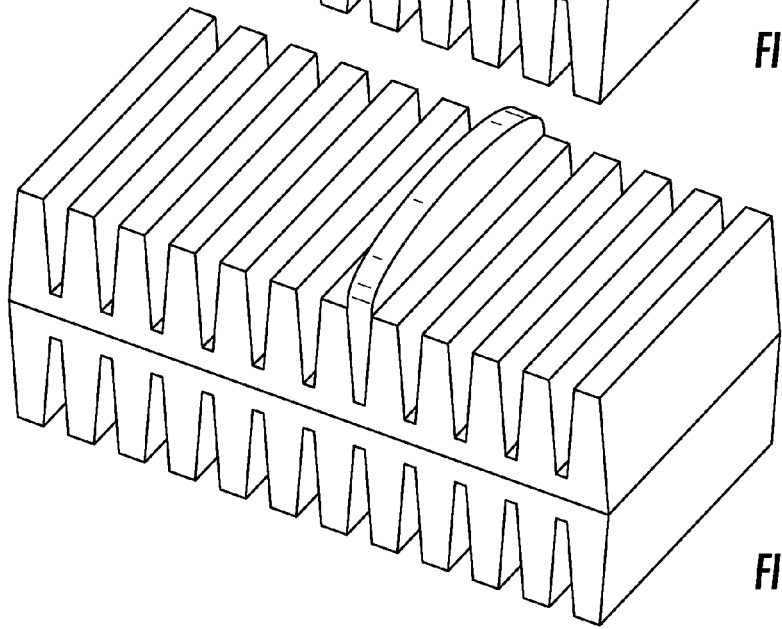
FIG. 33 is a perspective view of an air freshener cartridge having a handling feature.

Other embodiments of cartridges having handling features extending from the ribs of the cartridge body, past the height of the cartridge body, are illustrated in FIGS. 31, 32, and 33.

Air Freshener Systems & Methods

Air freshener systems and methods are also provided herein. In certain embodiments, an air freshener system include an air freshener dispenser having any features or combination of features described herein and a cartridge having a size and shape to fit in the cavity of the dispenser to provide the desired passive and/or fan-induced release of the air freshener substance.

In certain embodiments, as shown in FIG. 2, an air freshener system includes (i) a cartridge 120 having a body 148 including a polymer impregnated with an air freshening substance and having a volume of from about 0.4 in$^3$ (7,000 mm$^3$) to about 1.4 in$^3$ (23,000 mm$^3$) and a surface area of from about 9 in$^2$ (6,000 mm$^2$) o about 28 in$^2$ (18,000 mm$^2$), (ii) a housing 103 having a cavity 116 containing the cartridge 120, (iii) a fan 112 within the housing 103 that induces an airflow through the housing 103 and directs the airflow to an area outside of the housing 103, such that released air freshening substance is entrained in the airflow directed from the housing 103, (iv) a motor (not shown) within the housing 103 for driving the fan 112, (v) at least one sensor 122, 124, and (vi) a controller 114 within the housing 103 that receives a signal from the at least one sensor 122, 124 and directs operation of the fan 112 in response thereto.

In certain embodiments, as shown in FIG. 5, the air freshener system is configured such that the cavity 516 and cartridge 520 are sized and shaped to enable the cartridge 520 to be oriented in the cavity 516 with the airflow channels 552 of the cartridge 520 aligned with an airflow path 529 between the air inlet 528 and the fan 512. For example, as discussed above, the housing may include at least one projection within the cavity corresponding to one or more recesses of the cartridge. In some embodiments, the projection is configured to orient the cartridge in the cavity such that the airflow channels of the cartridge are aligned with an airflow path between the air inlet and the fan. In some embodiments, as discussed above, the projection(s) of the housing are configured to allow airflow thereby in the recess(es) of the cartridge, to appropriately maximize release of the air freshening substance from the cartridge body.

Thus, parameters of the system, including, but not limited to, the cartridge body composition (e.g., air freshening substance to matrix material ratio), the cartridge body size and shape (e.g., volume and surface area), the housing and cavity headspace volumes, and the volumetric air release rate and fan speed, may be selected to achieve a particular air freshener release profile for the system. For example, these parameters may be tailored, along with the above-described controller logic sequences, to achieve release of a consistent amount of air freshening substance to combat odor and/or provide fragrance over a desired lifetime of the cartridge, without depleting the cartridge too quickly or providing overwhelming or unpleasant fragrance release.

In certain embodiments, the system parameters are configured such that the lifetime of the cartridge in the air freshener dispenser at regular usage rates is from 7 days to 60 days. For example, the system may be configured such that the lifetime of the cartridge in the air freshener dispenser at regular usage rates is about 7 days, about 14 days, about 30 days, or about 60 days, depending on the desired maintenance schedule and other considerations.

In certain embodiments, the system parameters are configured such that the airflow containing the entrained, released air freshening substance is directed from the dispenser at a volumetric rate of from about 0.1 ft$^3$/min (0.003 m$^3$/min) to about 10 ft$^3$/min (0.3 m$^3$/min). In some embodiments, the airflow containing the entrained released air freshening substance is directed from the housing at a volumetric rate of from about 1 ft$^3$/min (0.03 m$^3$/min) to about 3 ft$^3$/min (0.09 m$^3$/min).

In certain embodiments, the cartridge has a surface area and other relevant design features sufficient to infuse the headspace of the cavity with air freshening substance released from the cartridge, such that within at least 30 seconds (e.g., from 10 to 25 seconds) the headspace is filled with the air freshening substance in the absence of the fan being driven. As used herein, the term "infuse" refers to filling the headspace with air freshening substance, accounting for passive diffusion of the air freshening substance to an area outside of the relevant volume (e.g., the cavity headspace or housing headspace). That is, the system may be configured such that the cartridge passively releases a sufficient volume of air freshening substance to infuse the cavity headspace within 30 seconds and thereby release a maximum amount of air freshening substance upon running the fan.

In certain embodiments, a kit is also provided, including an air freshener cartridge and an automated air freshener dispenser. For example, any suitable air freshener dispenser described herein along with a suitable cartridge configured to be loaded in the cavity of the dispenser may be provided as a kit of parts. In some embodiments, a kit includes (i) a cartridge having a body including a matrix material impregnated with an air freshening substance and having a volume of from about 0.1 in$^3$ (1,600 mm$^3$) to about 2.5 in$^3$ (41,000 mm$^3$) and a surface area of from about 2.0 in$^2$ (1,300 mm$^2$) to about 40 in$^2$ (26,000 mm$^2$), and (ii) an automated air freshener dispenser having a housing with a cavity for receiving the air freshener cartridge, a fan within the housing that induces an airflow through the housing and directs the airflow to an area outside of the air freshener dispenser, such that released air freshening substance is entrained in the airflow directed from the air freshener dispenser, a motor within the housing for driving the fan, at least one sensor; and a controller within the housing that receives a signal from the at least one sensor and directs operation of the fan in response thereto.

Methods for reducing malodor in a public washroom are also provided. These methods may include, for instance, (i) providing an air freshener dispenser as described in any embodiments, or combination of embodiments, described herein, (ii) detecting the presence of a user near a sensor and/or detecting a user-request for air freshener dispense, (iii) transmitting a signal from the sensor(s) to the controller to drive rotation of the fan and induce an airflow through the dispenser, and (d) directing airflow containing released air freshening substance from the air freshener dispenser.

EXAMPLES

Air freshener cartridges and dispensers having a variety of designs and parameters were manufactured and tested for performance characteristics, including fragrance intensity and air freshener longevity.

Example 1

A cartridge prototype having an asterisk-shaped cross section (hereinafter "Cartridge 1," see Table 1 for parameters) was manufactured and tested using a dispenser having a motor configured to drive a fan for a period of 15, 30, or 60 seconds, to induce an airflow through and/or around the cartridge to volatilize the air freshening substance contained therein and to dispense the airflow containing the released air freshening substance. The dispensers had either a small (0.1 in$^2$) or a large (1 in$^2$) airflow outlet open surface area. The fan was configured to run at 5000 rpm and to induce airflow from the dispenser at a rate of about 3 ft$^3$/min (0.09 m$^3$/min). The fan was run for the specified duration every 10 minutes and the intensity of the fragrance released on was determined by a panel of experts according to a 5-point scale (with "5" indicating the greatest fragrance intensity and a near overwhelming fragrance level, and "0" indicating no fragrance detected). Intensity values of 2-4 were considered acceptable fragrance levels.

Figure 34:
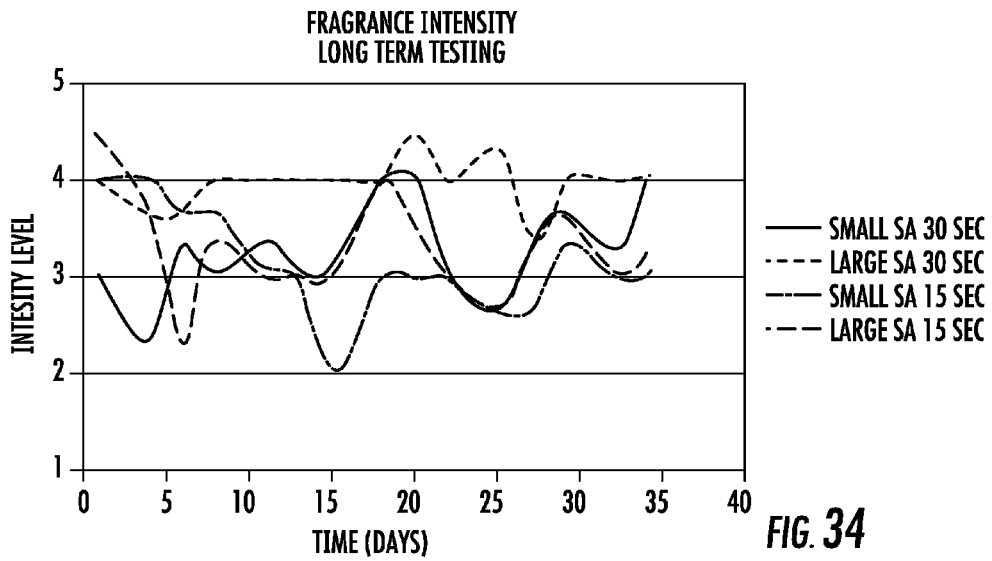
FIG. 34 is a graph showing fragrance intensity over time as measured in Example 1.

FIG. 34 shows the results of fragrance intensity and longevity testing performed on Cartridge 1 in dispensers having a small (0.1 in$^2$) and a large (1 in$^2$) airflow outlet open surface area (indicated as "small SA" and "large SA," respectively) with a fan being run for 30 seconds or 15 seconds, as indicated in the chart legend. As shown in FIG. 34, each of the dispenser-cartridge systems provided a fragrance intensity of between 2 to 4 and longevity of more than 30 days.

TABLE 1

| | Experimental Cartridge Parameters | | | |
|---|---|---|---|---|
| | Cartridge 1 (Asterisk-Shaped Prototype) | Cartridge 2 (FIG. 18A) | Cartridge 3 (FIG. 19A) | Cartridge 4 (FIG. 20A) |
| Composition | 25 wt % fragrance to 75 wt % polymer | 25 wt % fragrance to 75 wt % polymer | 25 wt % fragrance to 75 wt % polymer | 25 wt % fragrance to 75 wt % polymer |
| Surface Area (in$^2$) | 13.85 | 14.8 | 20.34 | 19.6 |
| Volume (in$^3$) | 0.95 | 0.95 | 0.94 | 0.76 |
| Surface Area/ Volume (in$^-$) | 14.6 | 15.6 | 21.6 | 25.8 |

TABLE 1-continued

Experimental Cartridge Parameters

|  | Cartridge 1 (Asterisk-Shaped Prototype) | Cartridge 2 (FIG. 18A) | Cartridge 3 (FIG. 19A) | Cartridge 4 (FIG. 20A) |
|---|---|---|---|---|
| Avg. Weight (g) | 14.44 | 12.9 | 13.3 | 11.42 |

Figure 35:
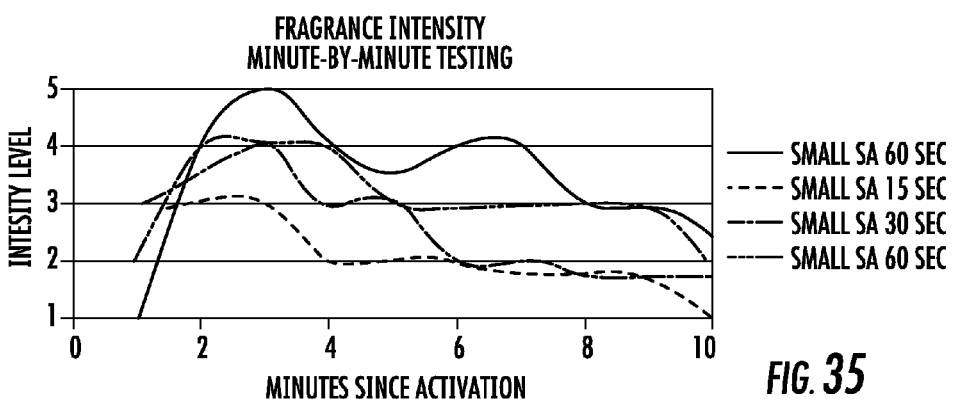
FIG. 35 is a graph showing fragrance intensity over time as measured in Example 1.

As shown in FIG. 35, minute-by-minute fragrance intensity testing was also performed with the fan being run for 15, 30, or 60 seconds with the small airflow outlet on the dispenser. The results show that the fragrance intensity peaks within the first few minutes of the fan being activated, but that the fragrance is present at an intensity of 2 or above for up to about 8 minutes thereafter. It was also determined that running the fan for 60 seconds for this experimental design produced a very high fragrance intensity that could be unpleasant to users, while running the fan for 15 seconds produced a low fragrance intensity.

Example 2

Based on the fragrance intensity and longevity data generated in Example 1, Cartridges 2, 3, and 4 were manufactured, to correspond generally to the cartridge body designs shown in FIGS. 18A, 19A, and 20A, respectively. Cartridge parameters (shown in Table 1) were selected to achieve similar air freshener release performance to Cartridge 1, based on the tests conducted in Example 1. Of these three cartridges, Cartridges 2 and 3 have similar designs, with different numbers of ribs and rib thicknesses. The parameters of Cartridge 2 most closely resemble those of Cartridge 1, while Cartridge 3 has a higher surface area but the same volume, and Cartridge 4 has a still higher surface area but decreased volume.

Figure 36:
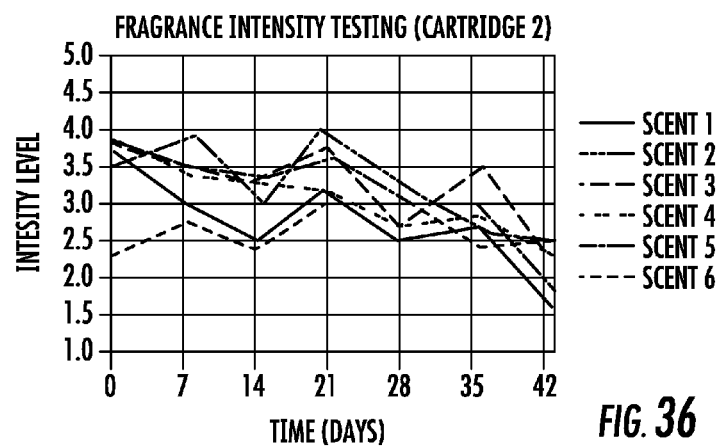
FIG. 36 is a graph showing fragrance intensity over time as measured in Example 2.
Figure 37:
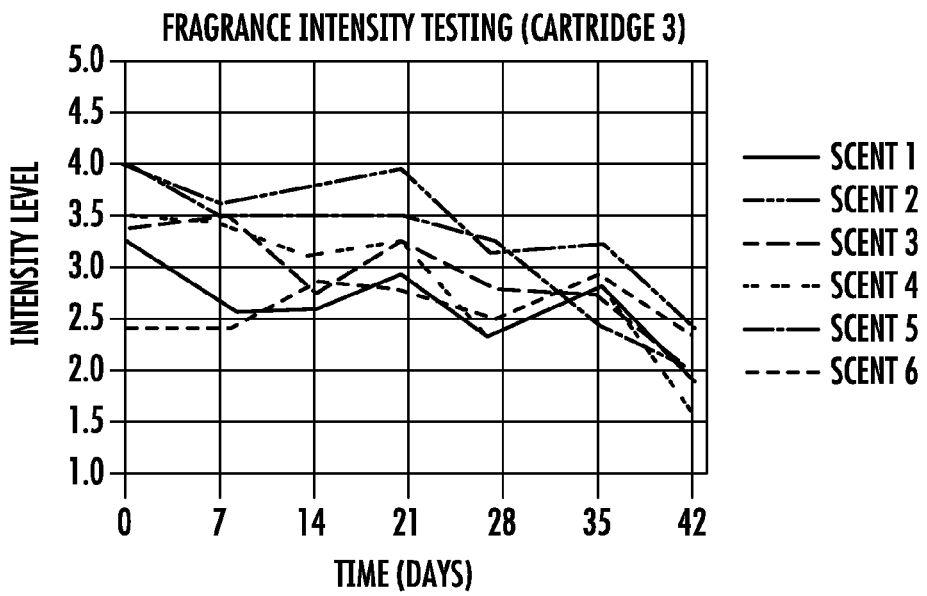
FIG. 37 is a graph showing fragrance intensity over time as measured in Example 2.

Fragrance intensity results of Cartridges 2 and 3, using six different fragrances are shown in FIGS. 36 and 37, respectively, over a six week test period with a fan run every 5 minutes (24 hours per day, 7 days per week) in a closed evaluation booth of approximately 290 cubic feet. The fragrance intensity was assessed weekly. After the fan is run, the intensity level of the fragrance was determined within 15 minutes. Results showed that Cartridge 2 and Cartridge 3 gave similar fragrance intensity performance for all six fragrances, with Cartridge 3 showing slightly higher fragrance intensity throughout. Thus, based on the Cartridge 2 and Cartridge 3 results, it was determined that having more surface area at a constant volume on the refill gives more fragrance intensity.

Figure 38:
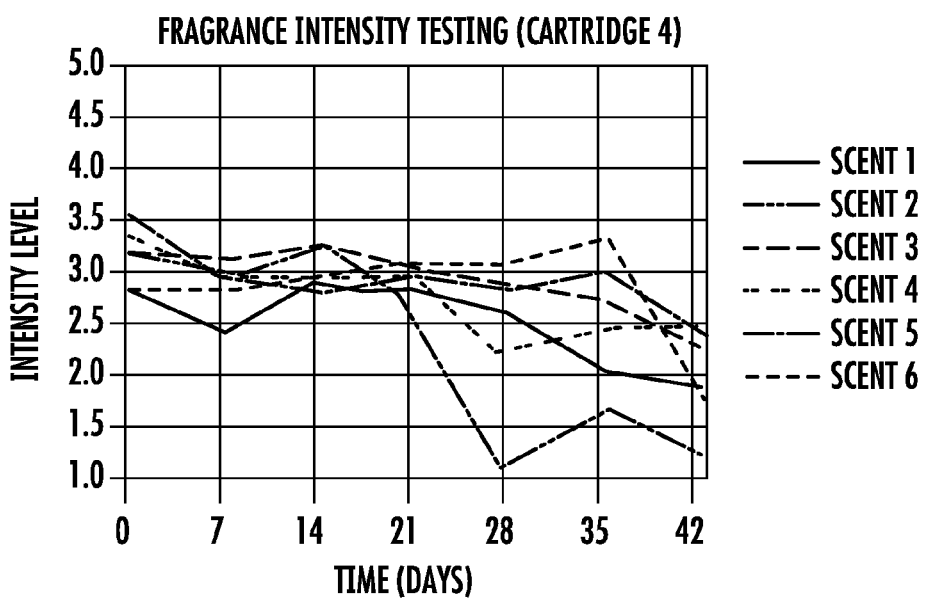
FIG. 38 is a graph showing fragrance intensity over time as measured in Example 2.

Cartridge 4 parameters were selected to test the effect of cartridge design as well as surface area and volume on fragrance intensity. Cartridge 4 has a different design than Cartridge 2 and Cartridge 3. Cartridge 4 contains wavy, serpentine ribs parallel to fan airflow whereas Cartridge 2 and Cartridge 3 have straight ribs parallel to fan airflow. Additionally, Cartridge 4 has a lower volume than Cartridges 2 and 3, thus having the highest surface area to volume ratio of the three Cartridge designs. Fragrance intensity results of Cartridge 4, using six different fragrances are shown in FIG. 38, over a six week test period, as described above.

Results using Cartridge 4 showed a slightly lower fragrance intensity performance for all six fragrances compared to Cartridges 2 and 3. Thus, the larger surface area to volume ratio of Cartridge 4 compared to those of Cartridges 2 and 3 unexpectedly did not produce stronger fragrance intensity. Thus, it was concluded that the lower fragrance performance of Cartridge 4 could be due to the wavy ridges of Cartridge 4 causing a restricted airflow around the refill for fragrance delivery. Therefore, cartridge design plays a significant role in attaining the desired fragrance release profile. Chemical compositions, physical properties of the fragrances, and refill design combined with mechanical parameters of the dispenser complete the fragrance delivery to achieve target performance.

Example 3

Figure 39:
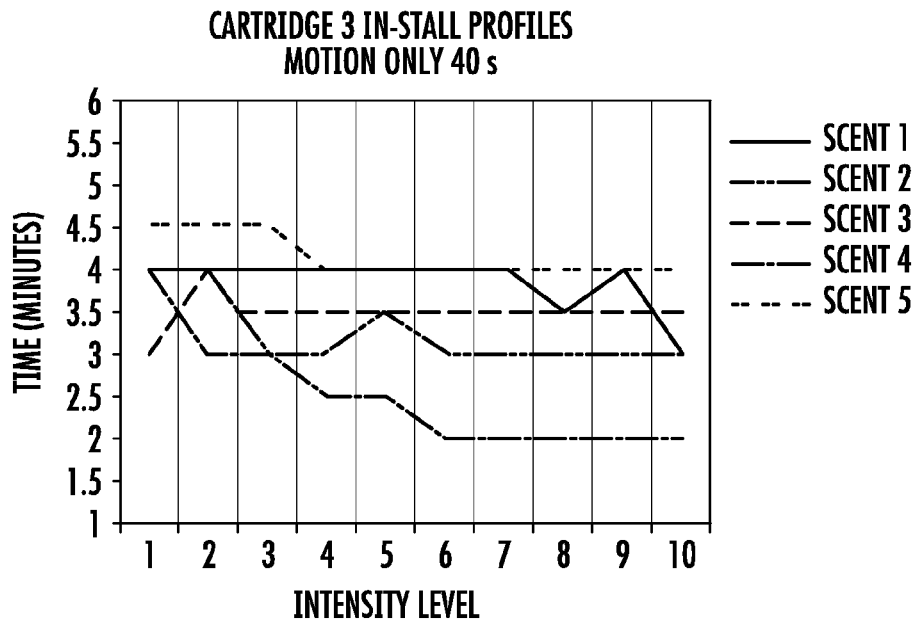
FIG. 39 is a graph showing fragrance intensity over time as measured in Example 3.
Figure 40:
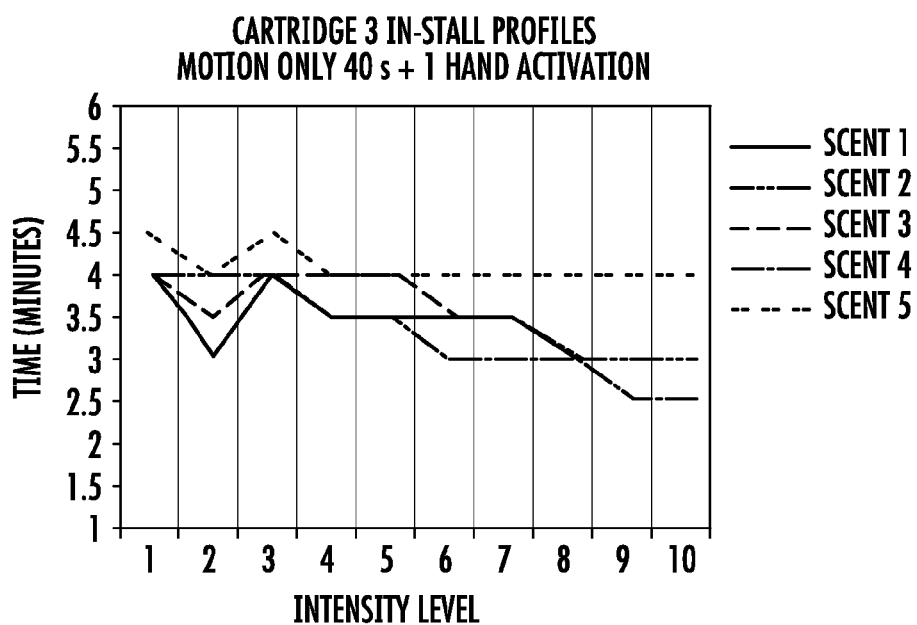
FIG. 40 is a graph showing fragrance intensity over time as measured in Example 3.

Various dispenser logic sequences were also tested for fragrance intensity performance. Specifically, Cartridges 2, 3, and 4 as described above were tested in a dispenser simulating a release in response to (A) motion activation and (B) motion activation followed by a user-request. The dispensers were located in a central stall of a multi-stall washroom. For logic sequence (A), the fan was run for 40 seconds. Evaluations of the fragrance intensity within the stall were determined at various times within 10 minutes of the fan being run. For logic sequence (B), the fan was run for 40 seconds, then was stopped for 60 seconds, then was run again for 20 seconds. Evaluations of the fragrance intensity within the stall were determined at various times within 10 minutes of the fan being run initially. The fragrance intensity data for logic sequence (A) are shown in FIG. 39 and the fragrance intensity data for logic sequence (B) are shown in FIG. 40.

Example 4

Figure 41:
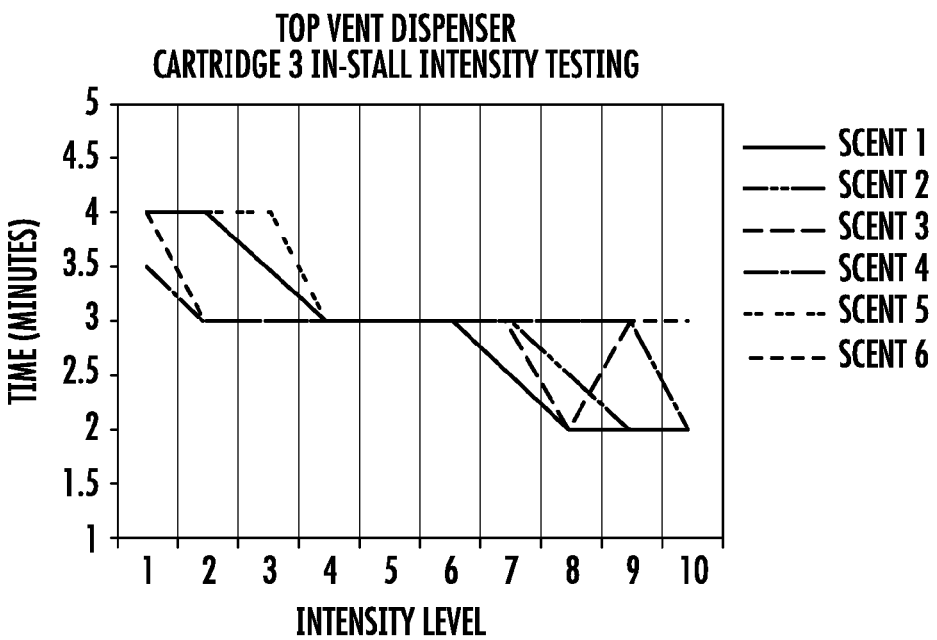
FIG. 41 is a graph showing fragrance intensity over time as measured in Example 4.
Figure 42:
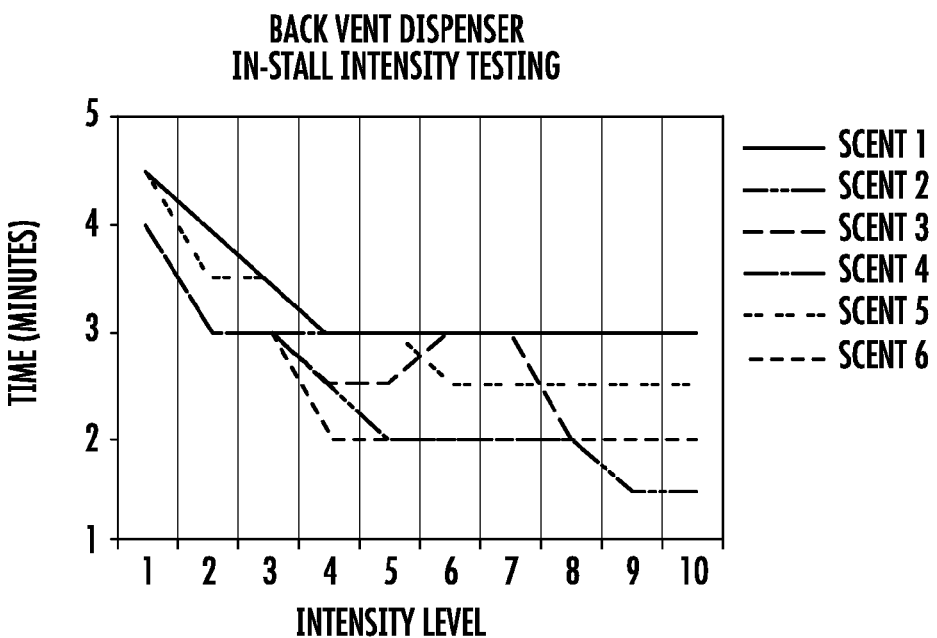
FIG. 42 is a graph showing fragrance intensity over time as measured in Example 4.

Passive vent locations on the dispenser were also tested. Specifically, dispensers having a top vent (e.g., a vent on the surface of the dispenser housing that is opposite the floor when the dispenser is installed on the wall) and a back vent (e.g., a vent on the surface of the dispenser adjacent the wall) to allow for passive diffusion of air containing passively released air freshening substance were tested with Cartridge 2. The results of these tests are shown in FIGS. 41 and 42, which show the measured fragrance intensity over time. These results indicate that open venting does allow for significant passive diffusion of the air freshening substance from the cartridge absent running of the fan, which lead to a more even fragrance release profile between fan activations.

Accordingly, air freshener dispensers, cartridges, and systems may be designed to achieve desired air freshener release in settings such as washrooms, washroom stalls, and other locations where malodor is a common issue. The air freshener dispensers, cartridges, and systems described herein may have one or more of the following benefits over currently available options: (1) improved effectiveness because the dispenser/freshener is closer to the source of the malodor; (2) improved effectiveness because washroom patrons can address instances of acute malodor through on-demand control; (3) easier refillability because the dispenser/freshener is positioned at a lower height than typical wall mounted devices; (4) easier maintenance because the dispenser/freshener does not require a liquid refill; and (5) improved cost effectiveness because the air freshener can be activated only when needed or requested.

While the disclosure has been described with reference to a number of example embodiments, it will be understood by those skilled in the art that the invention is not limited to such embodiments. Rather, the invention can be modified to incorporate any number of variations, alterations, substitutions, or equivalent arrangements not described herein, but which are commensurate with the spirit and scope of the invention. Additionally, while various example embodiments of the invention have been described, it is to be understood that aspects of the invention may include only some of the described embodiments. Accordingly, the invention is not to be seen as limited by the foregoing description, but is only limited by the scope of the appended claims.

We claim:

1. An air freshener system, comprising:
a cartridge comprising a body that comprises a matrix material impregnated with an air freshening substance for release selected from an odor-combatting composition, a fragrance, and a combination thereof, the body having a volume of from about 0.1 in$^3$ (1,600 mm$^3$) to about 2.5 in$^3$ (41,000 mm$^3$) and a surface area of from about 2.0 in$^2$ (1,300 mm$^2$) to about 40 in$^2$ (26,000 mm$^2$);
a housing that comprises a cavity containing the cartridge;
a fan within the housing that induces an airflow through the housing and directs the airflow to an area outside of the housing, such that released air freshening substance is entrained in the airflow directed from the housing;
a motor within the housing for driving the fan;
at least one sensor; and
a controller within the housing that receives a signal from the at least one sensor and directs operation of the fan in response thereto.

2. The air freshener system of claim 1, wherein the body comprises a plurality of ribs extending from a substrate and forming airflow channels therebetween.

3. The air freshener system of claim 2, wherein:
the housing further comprises an air inlet,
the cavity and cartridge are sized and shaped such that the cartridge is oriented in the cavity such that the airflow channels of the cartridge are aligned with an airflow path between the air inlet and the fan.

4. The air freshener system of claim 2, wherein:
the housing further comprises an air inlet,
the housing further comprises at least one projection within the cavity,
the cartridge comprises a recess configured for mating engagement with the projection of the housing, and
the projection is configured to orient the cartridge in the cavity such that the airflow channels of the cartridge are aligned with an airflow path between the air inlet and the fan.

5. The air freshener system of claim 4, wherein the at least one projection is configured to allow airflow thereby in the recess of the cartridge.

6. The air freshener system of claim 1, wherein the cavity has a headspace volume of from about 1 in$^3$ (20,000 mm$^3$) to about 4 in$^3$ (70,000 mm$^3$).

7. The air freshener system of claim 1, wherein the housing has a headspace volume of from about 15 in$^3$ (250,000 mm$^3$) to about 45 in$^3$ (740,000 mm$^3$).

8. The air freshener system of claim 1, wherein the airflow comprising the entrained released air freshening substance is directed from the housing at a volume of from about 0.1 ft$^3$/min (0.003 m$^3$/min) to about 10 ft$^3$/min (0.3 m$^3$/min).

9. The air freshener system of claim 1, wherein the cartridge has a surface area that is sufficient to infuse a headspace of the cavity with air freshening substance released from the cartridge every 30 seconds, in the absence of the fan being driven.

10. An automated air freshener dispenser, comprising:
a housing that comprises a cavity for receiving a cartridge comprising an air freshening substance for release;
a fan within the housing that induces an airflow through the housing and directs the airflow to an area outside of the air freshener dispenser, such that released air freshening substance is entrained in the airflow directed from the air freshener dispenser;
a motor within the housing for driving the fan;
at least one sensor; and
a controller within the housing that receives a signal from the at least one sensor and directs operation of the fan in response thereto,
wherein the housing of the air freshener dispenser is mountable to a bath tissue dispenser housing,
wherein the housing further comprises an air inlet and an airflow outlet through which the airflow comprising the entrained released air freshening substance is directed from the air freshener dispenser, and
wherein an airflow path from the air inlet to the airflow outlet is tortuous.

11. The air freshener dispenser of claim 10, wherein the housing of the air freshener dispenser is configured to be snap fit to the bath tissue dispenser housing.

12. The air freshener dispenser of claim 10, wherein the at least one sensor is selected from a group consisting of motion sensors, light sensors, malodor sensors, switches, and combinations thereof.

13. The air freshener dispenser of claim 10, wherein the housing further comprises an airflow outlet through which the airflow comprising the entrained released air freshening substance is directed from the air freshener dispenser.

14. The air freshener dispenser of claim 13, wherein the fan is positioned within the housing between the airflow outlet and the cavity.

15. The air freshener dispenser of claim 10, wherein the airflow comprising the entrained released air freshening substance is directed from the air freshener dispenser at a volume of from about 0.1 ft$^3$/min (0.003 m$^3$/min) to about 10 ft$^3$/min (0.3 m$^3$/min).

16. The air freshener dispenser of claim 10, wherein the controller directs the motor to drive the fan for a predetermined duration in response to receipt of a signal from the at least one sensor.

17. The air freshener dispenser of claim 10, wherein the controller further determines whether the fan has been driven within a predetermined period preceding receipt of a signal from the at least one sensor and prevents the motor from driving the fan in response to receipt of the signal if the fan has been driven within the predetermined period preceding receipt of the signal.

18. An automated air freshener dispenser, comprising:
a housing that comprises a cavity for receiving a cartridge comprising an air freshening substance for release;
a fan within the housing that induces an airflow through the housing and directs the airflow to an area outside of the air freshener dispenser, such that released air freshening substance is entrained in the airflow directed from the air freshener dispenser;
a motor within the housing for driving the fan;
at least one sensor; and
a controller within the housing that receives a signal from the at least one sensor and directs operation of the fan in response thereto,
wherein the housing comprises at least one projection within the cavity, the projection being configured for mating engagement with a recess of the cartridge and comprising a plurality of ribs or posts.

19. An automated air freshener dispenser, comprising:

a housing that comprises a cavity for receiving a cartridge comprising an air freshening substance for release;

a fan within the housing that induces an airflow through the housing and directs the airflow to an area outside of the air freshener dispenser, such that released air freshening substance is entrained in the airflow directed from the air freshener dispenser;

a motor within the housing for driving the fan;

at least one sensor; and a controller within the housing that receives a signal from the at least one sensor and directs operation of the fan in response thereto, wherein the housing comprises a door that provides access to the cavity, and wherein the housing comprises at least one projection within the cavity and located on the door, the projection being configured for mating engagement with a recess of the cartridge.

* * * * *